Figure 1:
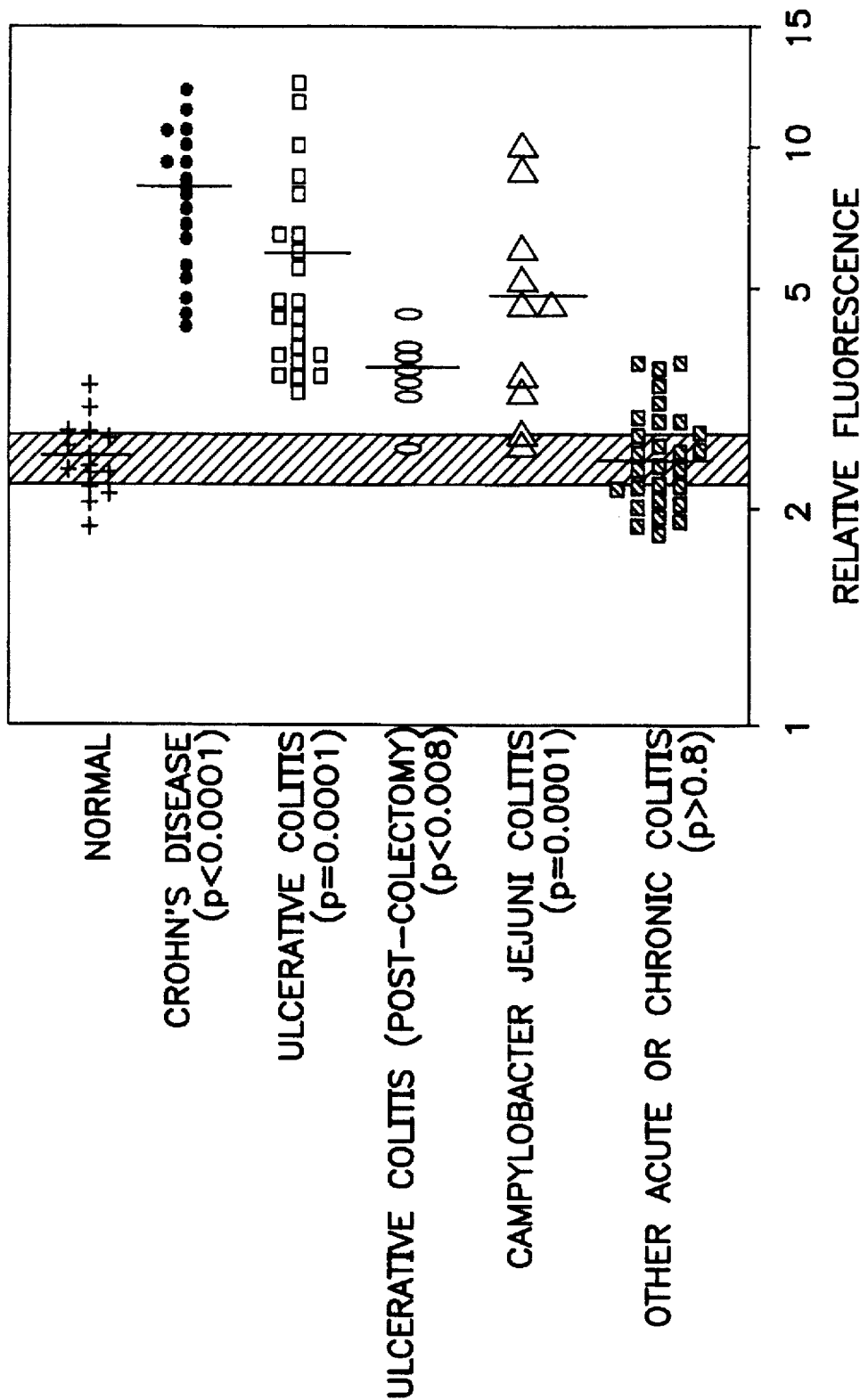

United States Patent [19]
Braun et al.

[11] Patent Number: 5,691,151
[45] Date of Patent: Nov. 25, 1997

[54] METHODS OF SCREENING FOR ULCERATIVE COLITIS AND CROHN'S DISEASE BY DETECTING VH3-15 AUTOANTIBODY AND PANCA

[75] Inventors: Jonathan Braun, Encino; Stephan R. Targan, Los Angeles, both of Calif.

[73] Assignee: Regents of University of California, Oakland, Calif.

[21] Appl. No.: 320,515

[22] Filed: Oct. 7, 1994

[51] Int. Cl.$^6$ .................................................. G01N 33/564
[52] U.S. Cl. .......................... 435/7.2; 435/7.24; 435/7.25; 435/7.32; 435/7.9; 435/7.95; 435/961; 435/965; 435/975; 436/506; 436/508
[58] Field of Search ........................ 435/7.2, 7.24, 435/7.25, 7.32, 7.9, 7.95, 961, 965, 975; 436/506, 508

[56] References Cited

U.S. PATENT DOCUMENTS 5,292,667  3/1994  Podolsky et al. ...................... 436/435

FOREIGN PATENT DOCUMENTS

| | | |
|---|---|---|
| 0286405 | 10/1988 | European Pat. Off. |
| 0615129 | 9/1994 | European Pat. Off. |
| WO8705703 | 9/1987 | WIPO |
| 9118628 | 6/1991 | WIPO |
| 9202819 | 7/1991 | WIPO |
| 9312248 | 12/1992 | WIPO |
| WO9307485 | 4/1993 | WIPO |

OTHER PUBLICATIONS

Berberian, L.S. et al., Journal of Immunology, "Expression of a Novel Autoantibody Defined by the $V_H$3-15 Gene in Inflammatory Bowel Disease and *Campylobacter jejuni* Enterocolitis", 153:(8):3756-3763 (1994).

Pallone, F. et al., J. Clin. Lab. Immunol., "Raised Serum Levels of IgM-Rheumatoid Factor And Anti-F(ab)2 Autoantibodies In Patients With Active Inflammatory Bowel Disease", 19(4):175-180 (1986).

Peter, H.H. et al., Journal of Interferon Research, "Novel Autoantibodies In Human Diseases", 14(4):153-155 (1994).

Adderson, E.E., et al., "Development of the Human Antibody Repertoire." *Pediatr. Res.*, 32(3): 257-263 (1992).

Cleveland, D. W., et al., "Peptide Mapping by Limited Proteolysis in Sodium Dodecyl Sulfate and Analysis by Gel Electrophoresis." *J. Biol. Chem.* 252(3): 1102-1106 (1977).

Lesavre, P., et al., "Atypical Autoantigen Targets of Perinuclear Antineutrophil Cytoplasm Antibodies (P-ANCA): Specificity and Clinical Associations." *J. Autoimmunity* 6: 185-195 (1993).

Perdigoto, R., et al., "Frequency and significance of chronic ulcerative colitis in severe corticosteroid-treated autoimmune hepatitis." *J. Hepatology* 14: 325-331 (1992).

Warny, M., et al., "Anti-neutrophil antibodies in chronic hepatitis and the effect of α-interferon therapy." *J. Hepatology* 17: 294-300 (1993).

Adderson, E.E., et al., "Restricted Ig H Chain V Gene Usage in the Human Antibody Response to *Haemophilus influenzae* Type b Capsular Polysaccharide." *J. Immunol.*, 147: 1667-1674 (1991).

Adderson, E. E., et al., "The Human VH3b Gene Subfamily Is Highly Polymorphic." *J. Immunol.*, 151(2): 800-809 (1993).

Adderson, E. E., et al., "Restricted Immunoglobulin VH Usage and VDJ Combinations in the Human Response to *Haemophilus influenzae* Type b Capsular Polysaccharide. Nucleotide Sequences of Monospecific Anti-*Haemophilus* Antibodies and Polyspecific Antibodies Cross-reacting with Self Antigens." *J. Clin. Invest.*, 91(6): 2734-2743 (1993).

Andris, J. S., et al., "Molecular Characterization of Human Antibodies to Bacterial Antigens: Utilization of the Less Frequently Expressed $V_H2$ and $V_H6$ Heavy Chain Variable Region Gene Families." *Mol. Immunol.*, 30: 1601-1616. (1993).

Axelrod, O., et al., "Idiotypic Cross-Reactivity of Immunoglobulins Expressed in Waldenström's Macroglobulinemia, Chronic Lymphocytic Leukemia, and Mantle Zone Lymphocytes of Secondary B-cell Follicles." *Blood*, 77: 1484-1490 (1991).

Berberian, L., et al., "Immunoglobulin $V_H3$ Gene Products: Natural Ligands for HIV gp120." *Science*, 261: 1588-1591 (1993).

Blaser, M. J., et al., "Studies of *Campylobacter jejuni* in Patients With Inflammatory Bowel Disease." *Gastroenterology*, 86: 33-38 (1984).

Blaser, M. J., et al., "*Camphyobacter jejuni* Outer Membrane Proteins Are Antigenic for Humans." *Infect. Immun.*, 43(3): 986-993 (1984).

Blaser, M. J., et al., "Human Serum Antibody Response to *Campylobacter jejuni* Infection as Measured in an Enzyme-Linked Immunosorbent Assay." *Infec. Immun.*, 44(2): 292-298 (1984).

Blaser, M. J., et al., "Antigenicity of *Campylobacter jejuni* Flagella." *Infec. Immun.*, 53(1): 47-52 (1986).

Braun, J., et al., "Restricted Use of Fetal VH3 Immunoglobulin Genes by Unselected B Cells in the Adult. Predominance of 56p 1-like VH Genes in Commom Variable Immunodeficiency." *J. Clin. Invest.*, 89: 1395-1402 (1992).

Chamberlain, C. E., et al., "*Campylobacter (Halicobacter) pylori*: Is Peptic Disease a Bacterial Infection?" *Arch. Intern Med.*, 150: 951-955 (1990).

Cook, G. P., et al., "A map of the human immunoglobulin $V_H$ locus completed by analysis of the telomeric region of chromosome 14q." *Nature Genet.*, 7(2): 162-168 (1994).

(List continued on next page.)

Primary Examiner—David Saunders
Attorney, Agent, or Firm—Campbell & Flores LLP

[57] ABSTRACT

The present invention provides novel methods of screening for ulcerative colitis and Crohn's disease which include the detection of two disparate autoantibodies: pANCA and VH3-15 autoantibody. The present invention also provides kits for screening ulcerative colitis and Crohn's disease.

66 Claims, 2 Drawing Sheets

OTHER PUBLICATIONS

Das, K.M., et al., "The Production and Characterization of Monoclonal Antibodies to A Human Colonic Antigen Associated with Ulcerative Colitis: Cellular Localization of the Antigen by Using the Monoclonal Antibody." *J. Immunology*, 139: 77–84 (1987).

Das, K. M., et al., "A Shared and Unique Epitope(s) on Human Colon, Skin, and Biliary Epithelium Detected by a Monoclonal Antibody." *Gastroenterology*, 98: 464–469 (1990).

Deane, M., et al., "The Genetic Basis of Human $V_H4$ Gene Family–Associated Cross–Reactive Idiotype Expression in CD5 + and CD5– Cord Blood B–Lympohocyte Clones." *Scand. J. Immunol.*, 38: 348–358 (1993).

Duerr, R. H., et al., "Anti–Neutrophil Crytoplasmic Antibodies in Ulcerative Colitis. Comparison With Other Colitides/Diarrheal Illnesses." *Gastroenterology* 100: 1590–1596 (1991).

Eggena, M., et al., "Characterization of Ulcerative Colitis Specific pANCA Using Phage Display Technology." *J. Amer. Soc. Exper. Biol.*, 8(5): A1010 (1994).

Elsaghier, A., et al., "Antibodies to *Mycobacterium paratuberculosis*–specific protein antigens in Crohn's disease." *Clin. Exp. Immunol.*, 90: 503–588 (1992).

Ermel, R. W., et al., "Preferential Utilization of a Novel Vlambda3 Gene in Monoclonal Rheumatoid Factors Derived From the Synovial Cells of Rheumatoid Arthritis Patients." *Arthritis Rheum.*, 37(6): 860–868 (1994).

Graham, D. Y., "*Campylobacter pylori* and Peptic Ulcer Disease." *Gastroenterology*, 96: 615–625 (1989).

Griffiths, A. D., et al., "Human anti–self antibodies wwith high specificity from phage display libraries." *EMBO J.*, 12: 725–734 (1993).

Huang, C., et al., "A Majority of Ig H Chain cDNA of Normal Human Adult Blood Lymphocytes Resembles cDNA for Fetal Ig and Natural Autoantibodies." *J. Immunol.*, 151: 5290–5300 (1993).

Jefferies, L. C., et al., "Idiotypic Heterogeneity of VkappaIII Autoantibodies to Red Blood Cell Antigens." *Clin. Immunol. Immunopathol.*, 65(2): 119–128 (1992).

Johnson, R. J., et al., "Persistent *Campylobacter jejuni* Infection in an Immunocompromised Patient." *Ann. Intern. Med.*, 100: 832–834 (1984).

Jonusys, A. M., et al., "IgM Natural Autoantibodies Against Bromelain–Treated Mouse Red Blood Cells Recognize Carbonic Anhydrase." *Autoimmunity*, 9: 207–216 (1991).

Kearney, J. F., "Idiotypic Networks." *Fundamental Immunology*. 3 ed. Paul, W. New York: Raven Press; 1993; c. 1993: 887–902. (Paul, W.). ISBN: 0–7817–0022–1.

Kipps, T. J., et al., "Uniform High Frequency Expression of Autoantibody–Associated Crossreactive Idiotypes in the Primary B Cell Follicles of Human Fetal Spleen." *J. Exp. Med.*, 171: 189–196 (1990).

Kipps, T. J., et al., "Autoantibodies in Chronic Lymphocytic Leukemia and Related Systemic Autoimmune Diseases." *Blood*, 81: 2475–2487 (1993).

Langman, R. E., et al., "The 'complete' idiotype network is an absurd immune system." *Immunol. Today*, 7: 100–103 (1986).

Lindberg, E., et al., "Antibody (IgG, IgA, and IgM) to baker's yeast (*Saccharomyces cerevisiae*), yeast mannan, gliadin, ovalbumin, and betalactoglobulin in monozygotic twins with inflammatory bowel disease." *Gut*, 33: 909–913 (1992).

Lydyard, P. M., et al., "The Antibody Repertoire of Early Human B Cells. III. Expression of Cross–Reactive Idiotopes Characteristic of Certain Rheumatoid Factors and Identifying VkappaIII, $V_H$I, and $V_H$III Gene Family Products." *Scand. J. Immunol.*, 32: 709–716 (1990).

Lynch, R. G., "Myeloma Proteins and Cells: Monoclonal Tools in the Analysis of Immunoregulatory Mechanisms." *Hybridoma*, 3: 60 (1984).

MacKenzie, L. E., et al., "Repertoire of CD5 + and CD5– cord blood B cells: specificity and expression of $V_H$I and $V_H$III associated idiotopes." *Clin. Exp. Immunol.*, 88(1): 107–111 (1992).

Mageed, R. A., et al., "Selective Expression of $V_H$IV Subfamily of Immunoglobulin Genes in Human CD5 + B Lymphocytes from Cord Blood." *J. Exp. Med.*, 174: 109–113 (1991).

Matsuda, F., et al., "Structure and physical map of 64 variable segments in the 3'0.8–megabase region of the human immunoglobulin heavy–chain locus." *Nature Genetics*, 3: 88–94 (1993).

Modlin, R. L., et al., "Type 2 cytokines and negative immune regulation in human infectors." *Curr. Opinion Immunol.* 5: 511–517 (1993).

O'Mahony,S., et al., "Systemic and mucosal antibodies to klebsiella in patients with ankylosing spondylitis and Crohn's disease." *Ann. Rheum. Dis.*, 51: 1296–1300 (1992).

Pascual, V., et al., "Human Immunoglobulin Heavy–Chain Variable Region Genes: Organization, Polymorphism, and Expression." *Adv. Immunol.*,49: 1–74 (1991).

Paul,W. E., et al., "Regulatory idiotopes and immune networks a hypothesis." *Immunol. Today*, 3: 230–234 (1982).

Pei, Z., et al., "Identification, Purification, and Characterization of Major Antigenic Proteins of *Campylobacter jejuni*." *J. Biol. Chem.*,266(25): 16363–16369 (1991).

Sanz, I., et al., "Nucleotide Sequences of Eight Human Natural Autoantibody $V_H$ Regions Reveals Apparent Restricted Use of $V_H$ Families." *J. Immunol.*, 142(11): 4054–4061 (1989).

Saxon, A., et al., "A distinct subset of antineutrophil cytoplasmic antibodies is associated with inflammatory bowel disease." *J. Allergy Clin. Immunol.*, 86: 202–210 (1990).

Siegel, D. L., et al., "Expression and Characterization of Recombinant Anti–Rh(D) Antibodies on Filamentous Phage: A Model System for Isolating Human Red Blood Cell Antibodies by Repertoire Cloning." *Blood*, 83(8): 2334–2344 (1994).

Stevens, T. R., et al., "Anti–Endothelial Cell Antibodies in Inflammatory Bowel Disease." *Digestive Dis. and Sci.*,38: 426–432 (1993).

Stewart, A. K., et al., "Immunoglobulin V Regions and the B Cell." *Blood*, 83(7): 1717–1730 (1994).

Tao, M., et al., "Idiotype/granulocyte–macrophage colony––stimulating factor fusion protein as a vaccine for B–cell lymphoma." *Nature*, 362: 755–758 (1993).

Tomlinson, I. M., et al., "The Repertoire of Human Germline $V_H$ Sequences Reveals about Fifty Groups of VH Segments with Different Hypervariable Loops." *J. Mol. Biol.*, 227: 776–798 (1992).

Towbin, H., et al., "Electrophoretic Transfer of Proteins from Polyacrylamide Gels to Nitrocellulose Sheets: Procedeure and Some Applications." *Proc. Natl. Acad. Sci. USA*, 76: 4350 (1979).

Valles–Avoub, Y., et al., "Characterization of a Common VH3–15 Autoantibody Relating Inflammatory Bowel Disease and *C. jejuni enterocolitis*." *J. Amer. Soc. Exper. Biol.*, 8(5): A1010 (1994).

Van Spreeuwel, J. P., et al., "Campylobacter colitis: histological immunohistochemical and ultrastructural findings." *Gut*, 26: 945–951 (1985).

Ward, E.S., et al., "Binding activities of a repertoire of single immunoglobulin variable domains secreted from *Escherichia coli*." *Nature*, 341: 544–546 (1989).

Yamamura, M., et al., "Defining Protective Responses to Pathogens: Cytokine Profiles in Leprosy Lesions." *Science*, 254: 277–279 (1991).

Yang, H., et al., "Ulcerative Colitis: A Genetically Heterogeneous Disorder Defined by Genetic (HLA Class II) and Subclinical (Antineutrophil Cytoplasmic Antibodies) Markers." *J. Clin. Invest.*, 92: 1080–1084 (1993).

Young, F., et al., "Molecular Analysis of a Germ Line–Encoded Idiotypic Marker of Pathogenic Human Lupus Autoantibodies." *J. Immunol.*, 145: 2545–2553 (1990).

METHODS OF SCREENING FOR ULCERATIVE COLITIS AND CROHN'S DISEASE BY DETECTING VH3-15 AUTOANTIBODY AND PANCA

I. ACKNOWLEDGEMENT

This invention was made with support under grant numbers DK46763 and CA12800 from the National Institute of Health. Accordingly, the United States Government has certain rights in the invention.

II. BACKGROUND OF THE INVENTION

A. The Antibody Repertoire

Over a lifetime, a person confronts the possibility of infection with an almost infinite number of unique foreign substances (antigens). Since it could never be anticipated which of these antigens will ultimately infect a person, it is beneficial that the body possesses an elegant system of producing an equally infinite array of antibodies which recognize, bind and trigger the destruction of antigens.

Antibodies are Y-shaped, tetrameric molecules consisting of a pair of identical, relatively long polypeptide chains called heavy (H) chains and a pair of identical, shorter polypeptide chains called light (L) chains. Each arm of the Y shaped structure is comprised of one light chain and one end of a heavy chain bound together by a single disulfide bond. At the juncture of the arms, the two heavy chains are bound to each other by two disulfide bonds to form the stem of the Y shaped structure.

This architectural description of an antibody, although visually appealing, can be deceptively simplistic. Antibody architecture accommodates a wealth of structural diversity. Both the heavy and light chains contain variable (V) and constant regions. These V regions are responsible for antigen binding.

Heavy and light chain variable regions (VH and VL) each consist of B-sheet scaffold, surmounted by three antigen-binding loops (complementarity-determining regions or CDRs) of different lengths which are fleshed with a variety of side chains. The CDRs are the most diverse regions of the antibody molecule; all six associate to one degree or another in forming the site at which the antibody binds its antigen (antigen-binding site). The structural diversity of the loops can create binding sites of a variety of shapes, ranging from almost flat surfaces to deep cavities.

Thus the vast array of antibody specificities depends on the diversity of V region structure which in turn depends on the diversity of the primary sequence of the V region. Underpinning the structural diversity of antibodies is a combinatorial genetic diversity. Heavy and light chain polypeptides are each encoded by an ensemble of gene segments selected from immunoglobulin (Ig) gene complexes. During the maturation of B-cell (the cells which produce antibodies), discontinuous gene segments within these gene complexes undergo a series of somatic rearrangements to form the nucleic acid sequence that ultimately may encode the heavy and light chains of the antibody molecule.

Generally, the first Ig gene rearrangements occur within the Ig heavy chain gene complex. The VH region is generated by the assembly of a VDJ exon from three separate germline DNA segments. One or more diversity (D) gene segments (selected from more than two dozen D germline gene segments) is joined with a single joining (JH) gene segment (selected from about six functional JH germline gene segments). The resulting DJH complex may then rearrange with a VH gene segment to form a VDJ exon that may encode the variable portion of the antibody heavy chain. About 120 germline VH gene segments (of which only about 80 are potentially functional) are available for Ig gene rearrangement and can be divided into at least six families in the basis of nucleotide homology of 80% or above. After successful VDJ rearrangement, a similar rearrangement occurs to produce the light chain.

Two of the heavy chain CDRs (1 and 2) are encoded by the VH segment. The heavy chain CDR3, the CDR in direct contact with antigen during antigen-antibody binding, is the most variable portion of the antibody molecule and is encoded by the 3' end of the VH gene segment, the D segment and the 5' end of the JH segment. With nucleotide addition (N-region diversity at the VH-D and D-JH junctions) the use of different reading frames in the D segment, and the combination of different rearranged heavy and light chains, the diversity of primary antibody libraries is huge. During an immune response, the antibody variable regions are further diversified by somatic hypermutation, leading to higher affinity binding of the antigen.

Contrary to what was first believed, that which may define the uniqueness of the antibody, idiotype, includes not only the antigen binding site (as was once believed) but also includes portions of the variable region that can be bound by other antibodies. It follows then that an idiotype of a given antibody molecule can be described as a collection of "idiotopes" as mapped by a panel of monoclonal anti-idiotypic antibodies, a conventional cross-absorbed polyclonal anti-idiotype antibody, binding of defined antigens or any combination of these.

B. Autoantibodies

The monumental repertoire of the adaptive immune system has evolved to allow it to recognize and ensnare virtually any shaped microbial molecule either at present in existence or yet to come. However, in doing so it has been unable to avoid the generation of autoantibodies, antibodies that bind with the body's own constituents and trigger an immunological path of destruction.

Natural immunological tolerance mechanisms prevent the expanded production of autoantibodies. After antibody gene rearrangement, virgin B-cells (the cells that generate antibodies) that display autoantibodies are destroyed or suppressed by the bodies tolerance mechanisms. Despite this safety-net, autoantibodies are still produced and for many people create no recognizable pathogenic disorder. It has been estimated that 10–30% of B cells in normal, healthy individuals are engaged in making autoantibodies. Production of autoantibodies is not only the result of an exceptionally diverse immune system, an immune response against one's self can also arise in autoimmune disease or after infections.

C. Inflammatory Bowel Disease, *Campylobacter jejuni* Enterocolitis And Primary Sclerosing Cholangitis

1. Inflammatory Bowel Disease

Inflammatory bowel disease (IBD) is the collective term used to describe two gastrointestinal disorders: ulcerative colitis (UC) and Crohn's disease (CD). Although the diseases have distinct pathophysiological characteristics, they are frequently considered together due to several clinical and therapeutic similarities. Excluded from this category, however, are gastrointestinal inflammatory disorders of known infectious, toxic or ischemic etiology which may mimic IBD acutely, but do not cause a chronic relapsing and remitting syndrome.

IBD occurs world-wide and is reported to afflict as many as two million people. The course and prognosis of IBD is widely variable. Onset has been documented at all ages; however, IBD predominately begins in young adulthood. The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD. 10% to 15% of all patients with IBD will require surgery over a 10-year period. The risk for the development of cancer is increased in patients with IBD as well, particularly in those with ulcerative colitis. The longer the duration of disease, the higher the risk of developing carcinoma. Patients with ulcerative colitis regularly undergo cancer surveillance by endoscopy after ten years of disease. Reports of an increasing occurrence of psychological problems, including anxiety and depression, are perhaps not surprising secondary effects of what is often a debilitating disease that occurs in people in the prime of life.

2. Methods of Diagnosing IBD

A battery of laboratory, radiological, and endoscopic evaluations are combined to derive a diagnosis of IBD and to assess the extent and severity of the disease. Nevertheless, differentiating UC from CD, as well as other types of inflammatory conditions of the bowel, such as irritable bowel syndrome, infectious diarrhea, rectal bleeding, radiation colitis, and the like, is difficult, because the mucosa of the small and large intestines reacts in a similar way to a large number of different insults. Once infectious-types of bowel disorders have been ruled out, the final diagnosis of IBD is often made on the basis of the progression of the disease. In many patients, though, the diagnosis of IBD must still be regarded as indeterminate because of the overlapping features of UC and CD, particularly with CD of the colon.

3. *Campylobacter jejuni* Enterocolitis Can Mimic IBD but Has Not Been Shown to be a Causative Factor Infection with *Campylobacter jejuni* has been reported to be the most common bacterial cause of acute diarrheal illness in developed countries. Campylobacter may cause a spectrum of intestinal diseases ranging from acute gastroenteritis to toxic megacolon, lymphadenitis mesenterialitis, and even appendicitis and cholecystitis. Usually infection with this organism results in acute gastroenteritis with fever and frequent loss of often bloody stools. The disease resolves spontaneously (although antibiotic-treatment is recommended) within about one week, but in 20% of patients it runs a more prolonged course and relapses resembling chronic IBD. Although *Campylobacter jejuni* enterocolitis may be indistinguishable from UC by endoscopic examination and histological examination of rectal biopsies can range from normal to inflammatory changes suggestive of acute infectious colitis or CD, it can be distinguished from IBD by any one of several serological tests or by culturing fecal specimens.

This mimicry of the pathological features of IBD, has spurred investigation into whether *Campylobacter jejuni* infection may be the cause or be a causative factor of IBD. Although these investigations do not unequivocally eliminate *Campylobacter jejuni* as pathogenically important to IBD, defined populations of IBD patients show that *Campylobacter jejuni* is not normally present in the intestinal flora and could not be found in CD patients during exacerbation. The reported conclusion from the data is that *Campylobacter jejuni* cannot be implicated as a cause of IBD.

4. Primary Sclerosing Cholangitis

Primary sclerosing cholangitis ("PSC"), is a chronic, progressive inflammatory disorder characterized by inflammation and fibrosis of the intrahepatic and extrahepatic bile ducts, which may occur in patients who also have a history of UC. The explanation for this clinical association is unknown. The course of the disease is generally one of slow progression to cirrhosis, portal hypertension and death from liver failure. Diagnosis is usually based on biochemical, radiological and histological criteria.

5. The Cause(s) of IBD are Unknown

Although the etiology of IBD is unknown, a number of studies have suggested that genetics is important in a person's susceptibility to IBD and that the immune system is responsible for mediating the tissue damage in these diseases. Generally speaking, a failure to down regulate the normal self-limited inflammatory response of the bowel is characteristic of IBD, but it remains unclear what initiates the pathogenic processes.

It has also been suggested that a primary abnormality of the immune system and its regulation might serve as primary initiating factors, or that the disease process might be initiated by an infectious agent and the injury is then perpetuated through immune-mediated or other processes. Although the mucosal injury observed during episodes of acute disease can resemble the effects of any of a number of recognized infectious agents, such as *Campylobacter jejuni* as discussed above, no transmissible infectious agent has been consistently identified with IBD.

Autoimmunity has been suggested in the pathogenesis of IBD. Evidence to suggest this hypothesis is based on the existence of circulating antibodies that react with unknown alimentary tract antigens of both human and animal origin. For example, human fetal and adult colonic, biliary, skin and vascular epithelial cells, epithelial cell associated components from murine small intestine, rat and human colonic epithelial glycoproteins, intestinal bacterial polysaccharide, and antigens from germ-free rat feces have been described to react with sera from patients with IBD. Other studies demonstrated an increased local IgG response in the colonic mucosa of patients with IBD and other colonic inflammations. The mechanism of this IgG response, the specific local antigens involved, and the role of these antibodies are unknown. While a wide range of immunologic abnormalities have been reported in these disorders, none other than the detection of perinuclear anti-neutrophil cytoplasmic antibodies ("pANCAs") in a biological sample appear to be sufficiently reliable to be of diagnostic value.

6. Need for Objective Diagnostic Tools

Inflammatory bowel disease poses a clinical and scientific challenge to physicians and researchers. To date most of the diagnostic tools for IBD are quite subjective. Diagnosis depends upon a host of procedures aimed at confirming the suspected diagnosis. The initial symptoms are often confused for non-chronic bowel disorders by physicians unfamiliar with IBD. Consequently, IBD often goes mistreated and undiagnosed until the disease shows its chronicity which results in referral of the patient to a specialist. The imprecise and subjective nature of endoscopic and radiologic examination can result in a misdiagnosis or indeterminate diagnosis even when the IBD is suspected. Unfortunately, the patient must often suffer as the disease progresses before a definitive diagnosis can be made.

The differentiation between the type of IBD, ulcerative colitis and Crohn's disease, carries important prognostic and therapeutic implications. For example, when colectomy is indicated, the type of IBD involved determines which surgical options are appropriate. Surgery (total colectomy) does represent a cure for the symptoms of UC, though a dramatic one. In CD, surgery is never curative. Continent procedures such as the ileorectal pull-through (mucosal proctectomy) or the Kock pouch may be desirable in UC, but are contraindicated in CD.

Thus, IBD and quite often its treatment affects the lifestyle and functional capabilities of those afflicted. Treatment courses often result in adverse physiologic manifestations which must be balanced against the therapeutic benefit. Any intervention which can improve patients' toleration of their disease and therapeutic program is welcome.

The availability of diagnostic methods that would readily distinguish UC from CD would represent a major clinical advance which would aid in therapeutic management of IBD and the design of more specific treatment modalities. In addition specific detection of the disease in prospective parents can be useful in genetic counseling. Accordingly, there has existed a need for convenient and reliable methods of screening for IBD for diagnostic, prognostic and therapeutic purposes.

III. BRIEF DESCRIPTION OF THE INVENTION

The present invention provides novel methods of screening for Crohn's disease ("CD") and ulcerative colitis ("UC") which include detection of two disparate autoantibodies: VH3-15 autoantibody and anti-neutrophil cytoplasmic autoantibody having cytoplasmic staining with perinuclear highlighting. These novel methods do not depend upon the presentation of clinical symptoms or the activity of the disease and provide a more sensitive method of screening for CD and UC than is provided by prior art methods.

Thus in accordance with the methods of the present invention, the amount of VH3-15 autoantibody in a sample from the patient is determined and the presence or absence of pANCA in a sample from the same patient is also detected. Crohn's disease is indicated by an amount of VH3-15 autoantibody in the sample which exceeds the amount of VH3-15 autoantibody in a VH3-15 assay control and the absence of pANCA. Ulcerative colitis is indicated by an amount of VH3-15 autoantibody in the sample that does not exceed the amount of VH3-15 autoantibody in a VH3-15 assay control and the presence of pANCA. The methods of the present invention are preferably performed using immunochemical reagents for example, anti-VH3-15 idiotypic antibody material, cell surface antigen, neutrophil, DNase-treated neutrophil and the like. Thus there are an array of different immunoassay formats in which the methods of the present invention may be performed.

Also provided by the present invention are kits for screening for UC and CD. Suitable kits include, for example, immunochemical reagents useful for determining the amount of VH3-15 autoantibody in a sample and the presence or absence of pANCA in a sample.

IV. BRIEF DESCRIPTION OF THE DRAWING

FIG. 1 is a graph reporting the results of sera from 101 subjects (see Table 3) which were analyzed for VH3-15 autoantibodies. Values are relative fluorescence intensities (the ratio of mean fluorescence for staining with anti-VH3-15 idiotypic antibody and buffer alone) for each subject in a disease group determined by flow cytometry as described in Example IV. Black bars are the mean values for all subjects in each disease group. The vertical stippled bar is the 90% confidence limits for values of the control group (healthy adults). P values compare each disease group to the control group.

Figure 2:
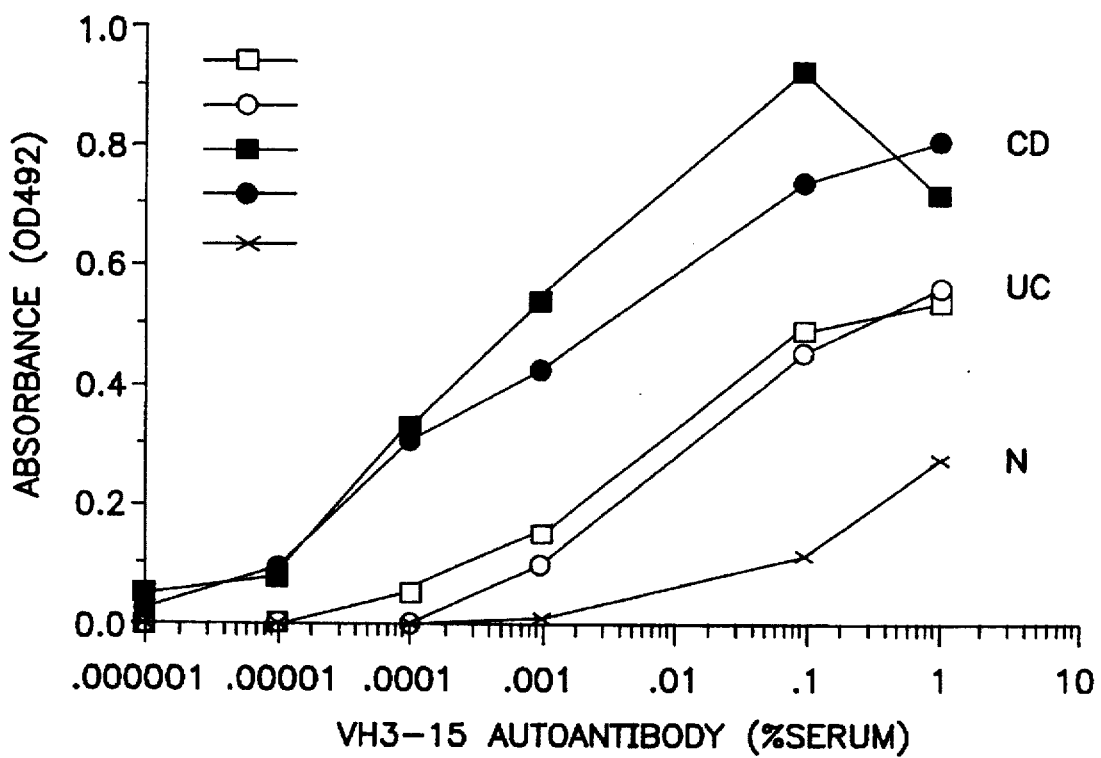

FIG. 2 is a graph reporting the results of two Crohn's disease patients, two ulcerative colitis patients and one normal tested for serum levels of VH3-15 autoantibody by fixed *Campylobacter jejuni* cell ELISA as described in Example VII.

V. DETAILED DESCRIPTION OF THE INVENTION

The monumental repertoire of the adaptive immune system has evolved to allow it to recognize and ensnare virtually any shaped microbial molecule either at present in existence or yet to come. However, in doing so it has been unable to avoid the generation of autoantibodies that bind with the body's own constituents and facilitate an immunological path of destruction.

By combining methods of detecting two disparate autoantibodies, VH3-15 autoantibody and anti-neutrophil cytoplasmic autoantibody having cytoplasmic staining with perinuclear highlighting, more sensitive screening methods for Crohn's disease ("CD") and ulcerative colitis ("UC") have been developed. These novel methods do not depend upon the presentation of clinical symptoms or the activity of the disease. High risk individuals, therefore, can be screened for the diseases prior to onset of clinical symptoms providing an opportunity for prognostic counseling, preventative intervention and genetic counseling.

The methods of the present invention are also useful for screening patients after onset of clinical symptoms, allowing physicians to diagnose these diseases earlier (instead of waiting for these diseases to show their chronicity), identify patients that may need additional testing and being therapeutic treatment earlier.

A. VH3-15 AUTOANTIBODY

Underpinning the structural diversity of antibodies is an elegant system of combinatorial genetic diversity in which an ensemble of gene segments, including a variable heavy (VH) gene segment, are joined together, subjected to mutation and expressed to produce a unique binding site with high affinity for one or more antigens. One manner in which an antibody can be identified is by the VH segment which it encodes.

Traditionally, VH gene segments that cross-hybridize by Southern filter hybridization under standard conditions (0.1× saturated sodium citrate, 0.1% sodium dodecyl sulfate, 65 degrees celsius) are considered members of the same VH gene family, whereas those VH gene segments that do not cross hybridize under these conditions are members of a distinct VH gene family. In practical terms this means approximately 80% nucleotide sequence homology places two genes within the same family and less than 70% nucleotide sequence homology classifies molecules as belonging to separate VH families. The VH3 gene family is presently considered to have the largest membership.

Recently, VH gene families have been subdivided into sub-families based upon homology to a germline sequence within a VH gene family. VH germline sequences have been mapped and the nomenclature for the sub-families reflects the locus of the germline gene segment. Thus, "VH3-15" refers to the fifteenth VH segment from the 3' end of the human Ig heavy chain locus. See, Matsuda, et. al., *Nature Genetics*, 3:88–94 (1993) incorporated herein by reference. The nucleic acid sequence of the VH3-15 gene segment is available on Genbank. The VH3-15 gene segment is also known as M26, 20p1, DP-38 and 9-1.

The term "VH3-15 nucleic acid sequence" as used herein refers to the nucleic acid sequence of a member of the VH3-15 sub-family. A nucleic acid sequence is a member of the VH3-15 sub-family if it has at least 92% nucleotide sequence homology with the VH3-15 germline gene segment. SEQ ID NO. 1, the nucleic acid sequence of 9-1 as reported in Pascual, et al, *Adv. Immun.*, 49:1–74 (1991) incorporated herein by reference, is provided as a representative example of a VH3-15 nucleic acid sequence. The nucleic acid sequence encoding LJ86 (SEQ ID NO. 4) is available on Genbank Accession No. M82929 and is also representative of a VH3-15 nucleic acid sequence. Additional VH3-15 nucleic acid sequences can be found in the published literature. See for example, Braun, et al., *J. Clin. Invest.*, 89:1395–1402 (1992), incorporated herein by reference.

The term "VH3-15 polypeptide" refers to a polypeptide sequence that encodes a member of the VH3-15 sub-family. A polypeptide sequence is a member of the VH3-15 sub-family if it is encoded by a VH3-15 nucleic acid sequence or if its CDR1 and CDR2 regions share at least 90% amino acid sequence homology with the CDR1 and CDR2 regions of SEQ ID NO. 3. SEQ ID NO. 2, 3 and 4 are representative of VH3-15 polypeptides.

The methods of the present invention include the detection of VH3-15 autoantibody. As used herein "VH3-15 autoantibody" refers to antibody molecules encoding a VH3-15 polypeptide and capable of binding proteinaceous antigen on the surface of erythrocyte cell membrane and *Campylobacter jejuni* cell membrane. More specifically, VH3-15 autoantibody is capable of binding surface-exposed erythrocyte cell membrane protein having a molecular weight of about 22,000 daltons on 12.6% SDS-PAGE, surface-exposed erythrocyte cell membrane protein having a molecular weight of about 28,000 daltons on 12.6% SDS-PAGE, surface-exposed *Campylobacter jejuni* cell membrane protein having a molecular weight of about 29,000 daltons on 10% SDS-PAGE, surface-exposed *Campylobacter jejuni* cell membrane protein having a molecular weight of about 50,000 daltons on 10% SDS-PAGE and surface-exposed *Campylobacter jejuni* cell membrane protein having a molecular weight of about 63,000 daltons on 10% SDS-PAGE. VH3-15 autoantibody is also capable of binding the monoclonal antibody produced by the hybridoma having ATCC Accession No. HB 11720. VH3-15 autoantibody is characterized in vivo as a serum antibody of predominately IgA, $IgG_1$, and IgG4 isotype found in humans diagnosed with IBD or infection by *Campylobacter jejuni*.

B. ANTI-NEUTROPHIL CYTOPLASMIC AUTOANTIBODY WITH PERINUCLEAR STAINING PATTERN

Patients with certain chronic inflammatory conditions have been found to have serum antibodies to cytoplasmic components of the neutrophil, ("ANCA"). By immunofluorescent microscopy, ANCA activity has been divided into two broad categories: cytoplasmic neutrophil staining ("cANCA") and cytoplasmic staining with perinuclear highlighting ("pANCA"). These distinct staining patterns are obtained with alcohol fixed cytocentrifuged neutrophils and represent an artifact of alcohol fixation. Nevertheless, this alcohol induced localization can serve to distinguish between types of ANCA.

As used herein, the term "pANCA" refers to anti-neutrophil cytoplasmic autoantibody characterized as having cytoplasmic staining with perinuclear highlighting and capable of binding antigen associated with cellular DNA of neutrophils. pANCA is further characterized as being associated with UC and primary sclerosing cholangitis ("PSC").

C. METHODS OF SCREENING FOR CROHN'S DISEASE AND ULCERATIVE COLITIS

In accordance with the present invention, there is provided methods of screening a patient for Crohn's disease and ulcerative colitis by determining the amount of VH3-15 autoantibody in a sample from the patient and detecting the presence or absence of pANCA in a sample from the same patient. Crohn's disease is indicated by an amount of VH3-15 autoantibody in the sample which exceeds the amount of VH3-15 autoantibody in a VH3-15 assay control and the absence of pANCA. Ulcerative colitis is indicated by an amount of VH3-15 autoantibody in the sample that does not exceed the amount of VH3-15 autoantibody in a VH3-15 assay control and the presence of pANCA. If the amount of VH3-15 autoantibody in the sample exceeds the amount of VH3-15 autoantibody in a VH3-15 assay control and pANCA is detected in the sample, IBD is indicated but the type of IBD remains indeterminant. Finally, a patient is considered not to have IBD if the amount of VH3-15 autoantibody in the sample does not exceed the amount of VH3-15 autoantibody in a VH3-15 assay control and pANCA is not detected. Table 1 summarizes the diseases indicated by results of the inventive method.

TABLE 1

| Disease state indicated by VH3-15 autoantibody and pANCA marker profile. | | |
|---|---|---|
| DISEASE STATE INDICATED | VH3-15 Autoantibody | pANCA |
| CD | + | − |
| UC | − | + |
| Indeterminant IBD | + | + |
| Non-IBD | − | − |

Eighty-one patients (27 each for non-IBD, ulcerative colitis, and Crohn's disease) were tested in accordance with a method of the present invention and in a blinded protocol. More specifically, serum samples from these eighty one patients were tested for the amount of VH3-15 autoantibody by "Fixed Erythrocyte ELISA" as described below and for the presence or absence of pANCA by "DNase-Treated, Fixed Neutrophil ELISA" as described below. A sample was positive for VH3-15 autoantibody if the sample contained an amount of VH3-15 autoantibody that exceed the VH3-15 autoantibody control by four standard errors of the mean. The results are summarized in Table 2.

TABLE 2

| Characterization of eighty-one patients of known disease state by VH3-15 autoantibody and pANCA. | | | | |
|---|---|---|---|---|
| VH3-15 Autoantibody | pANCA | Non-IBD | Ulcerative colitis | Crohn's Disease |
| − | − | 25 | 3 | 4 |
| − | + | 0 | 16 | 0 |
| + | − | 2 | 3 | 20 |
| + | + | 0 | 5 | 3 |

The majority of patients in each disease category have the characteristic autoantibody marker profile summarized in Table 1. Notably, by employing the method of the present invention in which CD and UC are indicated based upon both VH3-15 autoantibody status and pANCA status, sensitivity of the method is increased above the sensitivity obtainable when disease state is indicated by VH3-15 autoantibody status or pANCA status alone. In this particular sample, false positives for UC were reduced to zero and false positives for CD were reduced by 50%. False positives which would be attributable to PSC if pANCA status were the only indicator of UC and false positives attributable to infection by *Campylobacter jejuni* if VH3-15 autoantibody status were the only indicator of CD are also reduced when the methods of the present invention are employed.

The methods of the invention will now be described in terms of the component assays. For convenience of reference, the component of the method wherein the amount of VH3-15 autoantibody in a sample is determined will be referred to as the VH3-15 assay and the component of the assay wherein the presence or absence of pANCA is detected will be referred to as the pANCA assay.

1. Methods Of Determining the Amount Of VH3-15 Autoantibody in a Sample

In accordance with methods of the present invention, the amount of VH3-15 autoantibody in a sample is determined. Preferably, anti-VH3-15 idiotypic antibody material or cell surface antigen is employ as an immunochemical reagent to form an immune complex with any VH3-15 autoantibody which might be present in a sample. Even more preferably, both anti-VH3-15 idiotypic antibody material and cell surface antigen are employed. In this manner the amount of VH3-15 autoantibody in a sample is easily detected by detecting the amount of VH3-15 autoantibody-containing complex.

Of course, one of skill in the art will appreciate that there are various heterogenous and homogenous protocols, either competitive or noncompetitive, solution-phase or solid-phase, which can be employed in performing a VH3-15 assay method of this invention. Thus, while exemplary VH3-15 assay methods are described herein, the invention is not so limited.

In one embodiment of the invention, the amount of VH3-15 autoantibody in a sample can be determined by contacting a sample with cell surface antigen under conditions suitable to form an immune complex comprising cell surface antigen and VH3-15 autoantibody and detecting the amount of immune complex formed.

In another embodiment of the invention, the amount of VH3-15 autoantibody in a sample can be determined by contacting a sample with cell surface antigen and anti-VH3-15 idiotypic antibody material under conditions suitable to form an immune complex comprising cell surface antigen, VH3-15 autoantibody and anti-VH3-15 idiotypic antibody material, and detecting the amount of immune complex formed. The cell surface antigen and anti-VH3-15 idiotypic antibody material can be sequentially contacted with the sample or simultaneously contacted with the sample.

In accordance with the present invention, whether the amount of VH3-15 autoantibody detected in a sample exceeds the amount of VH3-15 autoantibody in a VH3-15 assay control can be simply determined, for example, by comparison to a VH3-15 assay control. The term "VH3-15 assay control" refers to the average amount of VH3-15 autoantibody detected in a sample from a patient without UC, CD and infection by *Campylobacter jejuni* ("normals").

Preferably, the VH3-15 assay control represents the average amount of VH3-15 autoantibody in the same type of sample from a normal patient which has been subjected to the same procedures and parameters as those used in the VH3-15 assay. For example, when the amount of VH3-15 autoantibody in a sample of human blood serum is determined by flow cytometry as described in Example IV, the VH3-15 assay control is most preferably defined as the average amount of VH3-15 autoantibody detected by flow cytometry in samples of human blood serum from normals. Thus, as that detection method is described in Example IV, the VH3-15 assay control is 2.5 and the patient is positive for the VH3-15 autoantibody if the amount of VH3-15 autoantibody in a human serum sample exceeds 2.5.

As a general guideline, the greater the amount VH3-15 autoantibody by which the test sample exceeds the VH3-15 assay control, the greater the assurance that the VH3-15 assay accurately represents a positive result for the VH3-15 autoantibody and in turn increases the sensitivity of the methods of the present invention. Thus, the sensitivity of the inventive method can generally be increase by requiring that the amount of VH3-15 autoantibody in the sample exceed the VH3-15 assay control by at least a given amount in order for the patient to be considered positive for the VH3-15 autoantibody. For example, when the amount of VH3-15 autoantibody in a sample of human blood serum is detected by flow cytometry as described in Example IV and the VH3-15 assay control is defined as 2.5, the sensitivity of the VH3-15 assay approaches 100% for CD and 90% for UC when a sample is only considered positive for the VH3-15 autoantibody if it exceeds the control by at least 0.75. Likewise, when an ELISA format is used to detect the amount of VH3-15 autoantibody in a sample, as described for example in Example VI and VII, absorbance for a panel of sera from normal subjects is determined. From this data, the mean (e.g., VH3-15 assay control) and preferably, the standard error of the mean ("SEM"), is calculated. If the amount of VH3-15 autoantibody in a sample, defined by absorbance in the ELISA format, exceeds the VH3-15 assay control by at least one SEM for the VH3-15 assay control, then the sensitivity for correctly detecting UC and CD in accordance with the methods of the present invention reaches 75%.

The VH3-15 assay control, as provided in the kits of the present invention for example, may take on many different physical forms. For example, a control can simply be a written expression of the average amount of VH3-15 autoantibody detected by a particular method in samples from normals or alternatively a statement that an amount in excess of a given amount detected in normals indicates that the patient sample is positive for the VH3-15 autoantibody. Alternatively, the VH3-15 assay control can be photograph of the results of the VH3-15 assay performed on a normal sample using a visually detectable marker which can be observed in a photograph. Preferably, the VH3-15 assay control is the same type of sample as the sample being tested and it has preferably been taken from a normal patient known to contain an average amount of VH3-15 autoantibody for normals and the control sample is subjected to the same procedure as the test sample.

A sample for purposes of conducting the VH3-15 assay can be obtained from any biological fluid or tissue containing that contains antibodies, for example, whole blood, plasma, biopsies of the colon, and the like, preferably serum. The same sample or the same type of sample may be used for the pANCA assay.

The term "cell surface antigen" as used herein refers to proteins and immunoreactive fragments of these proteins, that bind the antigen binding site of VH3-15 autoantibody and include, for example, proteins exposed on the surface of human erythrocyte cells that have a molecular weight of about 22,000 daltons or about 28,000 daltons on 12.6% SDS-PAGE, proteins exposed on the surface of *Campylobacter jejuni* cells that have a molecular weight of about 29,000 daltons, 50,000 daltons or 63,000 daltons on 10% SDS-PAGE.

Cell surface antigen useful in the practice of the present invention can be in non-purified or purified form. Thus, cell surface antigen can be bound to human erythrocyte cell membrane or *Campylobacter jejuni* cell membrane. If cell surface antigen bound to human erythrocyte cell membrane is used, preferably, the erythrocyte cell membrane is pretreated with bromelase to remove extraneous antigens.

As used herein, the term "purified" means that the molecule is substantially free of contaminants normally associated with a native or natural environment. For example, cell surface antigen can be purified of other constituents of the cell membrane. Methods of purifying antigens are well known in the art and include precipitation, affinity chromatography, solid or soluble phase immunoassays, and the like. These and other well known methods are described in Harlow and Lane, *Antibodies: A Laboratory Manual* (Cold Spring Harbor Laboratory 1988) incorporated herein by reference.

Alternatively, cell surface antigen and immunoreactive fragments thereof, can be obtained by well-known recombinant methods as described, for example, in Ausubel et al., *Current Protocols in Molecular Biology* (Greene Publishing Associates, Inc. and John Wiley & Sons, Inc. 1993), also incorporated herein by reference. An example of how these purified cell surface antigens and immunoreactive fragments can be obtained through recombinant means is to produce human reticulocyte cDNA library in the form of a surface expression vector such as pcDNA-1 (Invitrogen, San Diego, Calif.) cloned following the manufacture's directions. The library could then be expressed in COS cells and screened by flow cytometry or autoradiography using labeled VH3-15 autoantibody or anti-VH3-15 idiotypic antibody, such as for example, the monoclonal antibody produced by hybridoma having ATCC Accession No. HB 11720. See, H. Lin, et al., *Cell* 68:775-785 (1992), incorporated herein by reference. Cell surface antigen can also be purified and isolated through recombinant means by producing a *Campylobacter jejuni* cDNA library using the lambda gt11 vector (Stratagene, LaJolla, Calif.). Phage produced from this library could then be induced to express the gene insert and nitrocellulose filter contact replicas of plated phage plaques could be screened using labeled VH3-15 autoantibody or anti-VH3-15 idiotypic antibody.

These purified cell surface antigens and immunoreactive fragments thereof can also be produced by chemical synthesis. Synthetic proteins can be produced using Applied Biosystems, Inc. Model 430A or 431A automatic polypeptide synthesizer and chemistry provided by the manufacturer.

The term "anti-VH3-15 idiotypic antibody material" as used herein refers to antibody material capable of binding a variable heavy chain segment of a VH3-15 polypeptide, for example a variable heavy chain segment of VH3-15 autoantibody. Anti-VH3-15 idiotypic antibody material includes, for example, antibody material and monoclonal antibody molecules produced by hybridomas specifically identified in Example I as BK1, BK2, BK3, BK4, BK5, and BK7, as well as antibody material that bind the same idiotope as the monoclonal antibody molecules produced by these hybridomas. Hybridoma producing anti-VH3-15 idiotypic monoclonal antibody was deposited with American Type Culture Collection ("ATCC"), Rockville Md., on Sep. 26, 1994 and assigned ATCC Accession No. HB 11720 (referred to herein as BK2).

The term "antibody" or "antibody material" in its various grammatical forms is used herein as a collective noun that refers to an antibody molecule and immunologically active portions of an antibody molecule, i.e., molecules that contain an idiotope, antigen binding site, and the like.

The term "antibody molecule" in its various grammatical forms as used herein refers to an intact immunoglobulin molecule.

An "idiotope" in its various grammatical forms is used herein to refer to any portion of the variable region (heavy and light chain variable and hypervariable regions) of an antibody molecule that is capable of binding an antibody or an antigen. An "epitope" in its various grammatical forms is used herein refers to any portion of an antigen that is capable of binding an antibody. The word "epitope" will be reserved for use herein only to refer to antigenic determinants on non-immunoglobulin antigens.

Exemplary antibody material useful in the methods and kits of the present invention are intact immunoglobulin molecules, substantially intact immunoglobulin molecules and those portions of an immunoglobulin molecule that contain an idiotope, including those portions known in the art as Fab, Fab', F(ab')$_2$ and F(v). Fab and (Fab')$_2$ portions of antibodies are prepared by the proteolytic reaction of papain and pepsin, respectively, on substantially intact antibodies by methods that are well known in the art. See, for example, U.S. Pat. No. 4,342,566 to Theofilopolous and Dixon incorporated herein by reference. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

Whether anti-VH3-15 idiotypic antibody material is capable of binding a VH3-15 polypeptides can be measured by a variety of immunological assays known in the art, as described for example in Harlow and Lane, *Antibodies: A Laboratory Manual* (Cold Spring Harbor Laboratory 1988) incorporated herein by reference. Exemplary binding of an anti-VH3-15 idiotypic antibody with a VH3-15 polypeptide is described in Example II.

Anti-VH3-15 idiotypic antibodies of either monoclonal or polyclonal form can be produced using techniques presently known in the art. For example, polyclonal and monoclonal antibodies can be produced as described, for example, in Harlow and Lane, *Antibodies: A Laboratory Manual* (Cold Spring Harbor Laboratory 1988), which is incorporated herein by reference. Altered antibodies, such as chimeric, humanized, CDR-grafted or bifunctional antibodies can also be produced by methods well known to those skilled in the art. Such antibodies can also be produced by hybridoma, chemical or recombinant methodology described, for example in Ausubel et al., *Current Protocols in Molecular Biology* (Greene Publishing Associates, Inc. and John Wiley & Sons, Inc. 1993), also incorporated herein by reference. Exemplary methods of making and isolating monoclonal anti-VH3-15 idiotypic antibodies are provided in Examples I and II.

The phrase "monoclonal antibody" in its various grammatical forms refers to a population of antibody molecules that contain only one species of idiotope capable of immunoreacting with a particular epitope on an antigen or idiotope on an antibody. A monoclonal antibody typically displays a single binding affinity for an epitope or idiotope with which it immunoreacts; however, a monoclonal antibody may be a molecule having a plurality of idiotopes, each immunospecific for a different epitope or idiotope, e.g., a bispecific monoclonal antibody.

Monoclonal antibodies are typically composed of antibodies produced by clones of a single cell called a hybridoma that secretes (produces) but one kind of antibody molecule. One of skill in the art will recognize that the hybridomas disclosed herein can be used to produce other immortal cell lines that produce antibody material useful in the methods and kits of the present invention.

A hybridoma cell is formed by fusing an antibody-producing cell and a myeloma or other self-perpetuating cell line. The preparation of such hybridomas was first described by Kohler and Milstein, Nature, 256:495–497 (1975), which description is incorporated by reference. Polypeptide-induced hybridoma technology is also described by Niman et al., Proc. Natl. Sci. U.S.A., 80:4949–4953 (1983), which description is also incorporated herein by reference.

To obtain an antibody-producing cell for fusion with an immortalized cell, a mammal is inoculated with an immunogen. The word "immunogen" in its various grammatical forms is used herein to describe a composition containing a VH3-15 polypeptide as an active ingredient used for the preparation of the antibodies against VH3-15 polypeptides. When a polypeptide is used in an immunogen to induce antibodies, it is to be understood that the polypeptide can be used in various embodiments, e.g., alone or linked to a carrier as a conjugate, or as a polypeptide polymer or as a fusion protein for ease in purification. For a VH3-15 polypeptide that contains fewer than about 35 amino acid residues, the peptide may be bound to a carrier, for the purpose of inducing the production of antibodies.

The amount of VH3-15 polypeptide immunogen used to inoculate the mammal should be sufficient to induce an immune response to the immunizing polypeptide. This amount depends, among other things, on the species of animal inoculated, the body weight of the animal and the chosen inoculation regimen as is well known in the art. Inocula typically contain about 10 micrograms of immunogen per inoculation for mice and may contain up to about 500 milligrams of immunogen per inoculation for larger mammals.

The spleen cells of the mammal immunized with a VH3-15 polypeptide are then harvested and can be fused with myeloma cells using polyethylene glycol (PEG) 1500. Fused hybrids are selected by their sensitivity to HAT. Hybridomas producing an anti-VH3-15 idiotypic monoclonal antibody can be identified by screening hybridoma supernates for the presence of antibody molecules that immunoreact with VH3-15 polypeptide. Such screening methods include for example, radioimmunoassay (RIA) or enzyme linked immunosorbent assay (ELISA).

Anti-VH3-15 idiotypic monoclonal antibody can also be produced by initiating a monoclonal hybridoma culture comprising a nutrient medium containing a hybridoma that secretes anti-VH3-15 idiotypic antibody molecules. The culture is maintained under conditions and for a time period sufficient for the hybridoma to secrete the antibody molecules into the medium. The antibody-containing medium is then collected. The antibody molecules can then be further isolated by well known techniques.

Other methods of producing a monoclonal antibody, a hybridoma cell, or a hybridoma cell culture are also well known. See, for example, the method of isolating monoclonal antibodies from an immunological repertoire as described by Sastry et al., Proc. Natl. Acad. Sci., 86:5728–5732 (1989); and Huse et al., Science, 246:1275–1281 (1981), both of which are incorporated herein by reference.

Media useful for the preparation of these compositions are well known in the art and commercially available and include synthetic culture media, inbred mice and the like. An exemplary synthetic medium is Dulbecco's minimal essential medium (DMEM; Dulbecco et al., Virol., 8:396 (1959)) supplemented with 4.5 gm/l glucose, 20 mm glutamine, and 20% fetal calf serum. An exemplary inbred mouse strain is the Balb/c.

The terms "immune complex" and "immunocomplex" as used herein with regard both to the VH3-15 assay and the pANCA assay refers to the product of a specific binding reaction such as for example that between an epitope and an antigen binding site, between idiotope and an anti-idiotypic antibody, and the like. The term "VH3-15 autoantibody-containing complex" refers to an immune complex including at least VH3-15 autoantibody and will typically also include cell surface antigen and/or anti-VH3-15 idiotypic antibody material.

The VH3-15 assays of the present invention are typically performed at or below room temperature at about physiological pH. Because the methods involve the use of proteins, substantially higher temperatures acidity or alkalinity which would substantially modify the tertiary and quaternary structures of the proteins should be avoided. Accordingly, conditions suitable for performing the methods of the present invention generally range from about 1° C. to about 37° C., at about physiological pH. The time for performing the methods, of course, will decrease in relation to the increase in temperature at which the methods are performed.

Thus, for example, "conditions suitable to form" an immune complex comprising cell surface antigen and VH3-15 autoantibody comprise contacting cell surface antigen with human blood serum sample at about physiological pH at a temperature in the range of about 4° C. to about 37° C. for about 5 minutes to about 120 minutes, or preferably at a temperature in the range of about 20° C. to about 37° C. for about 5 minutes to about 60 minutes, and even more preferably at about room temperature for about 25 minutes to about 35 minutes. Conditions suitable to form an immune complex comprising cell surface antigen, VH3-15 autoantibody and anti-VH3-15 idiotypic antibody material further comprise contact the cell surface antigen/VH3-15 autoantibody immune complex with anti-VH3-15 idiotypic antibody material at about physiological pH, at a temperature in the range of about 1° C. to about 15° C. for about 5 minutes to about 120 minutes, or more preferably at a temperature in the range of about 5° C. to about 10° C. for about 10 minutes to about 60 minutes, or even more preferably by contacting them on ice for about 30 minutes In a presently preferred embodiment, the amount of VH3-15 autoantibody in a sample can be determined by contacting bromelase-treated human type O erythrocyte cell membrane with human blood serum at about room temperature for about 25 minutes to about 35 minutes at about physiological pH and then contacting the cell membrane and serum with detectably labeled monoclonal antibody produced by hybridoma having ATCC Accession No. HB 11720, on ice at about physiological pH for about 30 minutes.

In still another embodiment of the present invention, any immune complex formed by contacting sample with cell surface antigen or cell surface antigen and anti-VH3-15 idiotypic antibody material in the VH3-15 assay is separated from any uncomplexed cell surface antigen, uncomplexed anti-VH3-15 idiotypic antibody material and/or uncomplexed sample prior to determining the amount of immune complex. Methods of separating immune complex from uncomplexed material are well known in the art. When appropriate, a simple washing with a suitable buffer followed by filtration or aspiration is sufficient. If cell surface antigen or anti-VH3-15 idiotypic antibody material is immobilized on a particulate support, as in the case of microparticles for example, it may be desirable to centrifuge the particulate material, followed by removal of wash liquid. If cell surface antigen or anti-VH3-15 idiotypic antibody material is immobilized on membranes or filters, applying a vacuum or liquid absorbing member to the opposite side of the membrane or filter allows one to draw the wash liquid through the membrane or filter.

In presently preferred embodiments of the VH3-15 assay, cell surface antigen or anti-VH3-15 idiotypic antibody material is immobilized on a solid matrix. The solid matrix can be any support useful in immunometric assays. The matrix can be made from natural or synthetic material which is insoluble in water and can be rigid or non-rigid. However, the matrix should not significantly affect the desired activity of the cell surface antigen or anti-VH3-15 idiotypic antibody material. Preferred substrates include glass slides, test wells made from polyethylene, polystyrene, nylon, nitrocellulose, glass and the like. Also useful are test tubes, filter paper, filtering devices such as glass membranes, beads, and particulate materials such as agarose, cross-linked dextran and other polysaccharides, and the like.

In yet another embodiment of the present invention, cell surface antigen or anti-VH3-15 idiotypic antibody material employed in the VH3-15 assay is labeled with a detectable marker. Immune complex can then be indirectly and conveniently detected and quantified by detecting for example, enzymatic conversion, radioactivity, fluorescence, color and the like generated complexed, detectably-labeled cell surface antigen or anti-VH3-15 idiotypic antibody material.

Methods of labeling the compositions useful in the methods and kits of the present invention are well known in the art and contemplated as within the scope of the present invention. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981) incorporated herein by reference. The techniques of protein conjugation or coupling through activated functional groups are applicable (See, for example, Aurameas et al., *Scand. J. Immunol.*, Vol. 8, Suppl. 7:7–23 (1978), Rodwell et al., *Biotech.*, 3:889–894 (1984), U.S. Pat. No. 4,493,795 and J. H. Kennedy et al., *Clin. Chim. Acta*, 70:1 (1976) all of which are incorporated herein by reference.) and the specific use of biotin/avidin for labeling the compositions useful in the present invention is exemplified.

As used herein, the word "marker" in its various grammatical forms refer to single atoms and molecules that are either directly or indirectly involved in the production of a detectable signal to indicate the presence of a complex. Any marker can be linked to or incorporated in an expressed protein, polypeptide fragment, or antibody molecule that is part of an antibody or monoclonal antibody composition of the present invention, or used separately. These atoms or molecules can be used alone or in conjunction with additional reagents. Such labels are themselves well-known in clinical diagnostic chemistry and constitute a part of this invention only insofar as they are utilized with otherwise novel proteins, methods, and/or systems.

The detectable marker can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB-200-SC), phycoerythrin and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference. Alternatively, secondary antibody linked to fluorogen useful for the practice of the present invention may be obtained from a number of commercially available sources, for example, goat F(ab')2 anti-human IgG-FITC available from Tago Immunologicals, Burlingame, Calif.

Radioactive elements are also useful detectable markers. An exemplary radiolabeling agent is a radioactive element that produces gamma ray emissions. Elements which themselves emit gamma rays, such as $^{124}$I, $^{125}$I, $^{126}$I, $^{131}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such as $^{111}$indium or $^{3}$H.

In one embodiment, the detectable marker is an enzyme, such as horseradish peroxidase (HRP), glucose oxidase, and the like. In such cases where the detectable marker is an enzyme such as HRP or glucose oxidase, additional reagents are required to visualize the fact that an immune complex has formed. Such additional reagents for HRP include hydrogen peroxide and an oxidation dye precursor such as diaminobenzidine, o-phenylenediamine dihyrochloride and the like. An additional reagent useful with glucose oxidase is 2,2'-azino-di-(3-ethyl-benzthiazoline-G-sulfonic acid). Alternatively, secondary antibody linked to a detectable enzyme useful for the methods and kits of the present invention may be obtained from a number of commercially available sources, for example, goat F(ab')2 anti-human IgG-alkaline phosphatase may be purchased from Jackson Immuno-Research, located in West Grove, Pa.

Depending on the nature of the label or catalytic signal producing system used, a signal can be detected by irradiating the complexed test sample with light and observing the level of fluorescence; by contacting the complexed sample with a substrate which can be catalytically converted by the label to produce a dye, fluorescence or chemiluminescence, in which the formation of dye can be observed visually or in a spectrophotometer; fluorescence can be observed visually or in a fluorometer; or, in the case of chemiluminescence or a radioactive label, by employing a radiation counter such as a gamma counter or gamma emitting markers such as iodine-125. For detection of enzyme-catalyzed markers when the presently preferred combination of HRP is used as the enzyme and o-phenylenediamine dihydrochloride as the substrate, a quantitative analysis of complex can be made using a spectrophotometer, for example a EMAX Microplate Reader (available from Molecular Devices, Menlo Park, Calif.), at 492 or 405 nm in accordance with the manufacturer's instructions.

Specific binding agent are also useful as detectable markers. A "specific binding agent" is a molecular entity capable of selectively binding anti-VH3-15 idiotypic antibody material, cell surface antigen in purified or unpurified form, or a complex containing these. Exemplary specific binding agents are secondary antibody molecules (e.g., anti-Ig antibodies), complement proteins or fragments thereof, and the like which may themselves be labeled with a detectable marker. If one or more specific binding agents in the form of secondary antibody molecules is used, each secondary antibody molecule is preferably species-specific for the antibody or antigen it binds. Accordingly, in a preferred embodiment of the present invention, anti-VH3-15 idiotypic antibody material is detectably labeled by contacting it with specific binding agent, preferably labeled, specie-specific antibody molecule under conditions suitable to form a complex of anti-VH3-15 idiotypic antibody material and the specific binding agent. For example, when the monoclonal antibody produced by the hybridoma having ATCC Accession No. HB 11720 is employed as the anti-VH3-15 idiotypic antibody material, labeled anti-mouse specific for IgG isotype can be used as a specific binding agent.

2. Methods Of Detecting the Presence or Absence of pANCA in a Sample

In accordance with methods of the present invention, the presence or absence of pANCA in a sample is detected. Preferably, neutrophil and a specific binding agent for pANCA are employed as immunochemical reagents to form an immune complex with pANCA present in a sample. In this manner the presence or absence of pANCA in a sample can then be easily detected by detecting the presence or absence of the immune complex. Even more preferably, the pANCA assay also includes the use of DNase-treated neutrophil, wherein the presence of pANCA is detected by a loss of a detectable immune complex.

One of skill in the art will appreciate that there are various heterogenous and homogenous protocols, either competitive or noncompetitive, solution-phase or solid-phase, which can be employed in performing a pANCA assay method of this invention. Thus, while exemplary pANCA assay methods are described herein, the invention is not so limited.

In one embodiment of the invention, the presence or absence of pANCA in a sample is detected by contacting a sample with neutrophil and a specific binding agent under conditions suitable to form an immune complex comprising neutrophil, pANCA and the specific binding agent. In this embodiment as with the others, neutrophil and specific binding agent for pANCA can be sequentially contacted with the sample or simultaneously contacted with the sample. The presence or absence of the immune complex is then detected, wherein the presence of immune complex indicates the presence of pANCA in the sample and the absence of immune complex indicates the absence pANCA in the sample.

In a preferred embodiment of the invention, the presence or absence of pANCA in a sample is detected by (a) contacting a sample with neutrophil and a specific binding agent for pANCA under conditions suitable to form an immune complex comprising neutrophil, pANCA and the specific binding agent, (b) detecting the presence or absence of the immune complex formed in step (a), wherein the absence of immune complex indicates the absence of pANCA in the sample, (c) contacting a second sample with DNase-treated neutrophil and a specific binding agent for pANCA under conditions suitable to form an immune complex comprising DNase-treated neutrophil, pANCA and the specific binding agent, and (d) detecting the presence or absence of immune complex formed in step (c) wherein the presence of an immune complex in step (b) and the absence of an immune complex in step (d) indicates the presence of pANCA in the sample.

In another embodiment of the invention, pANCA is detected in the pANCA assay by indirect immunofluorescence. As described for example in Examples VIII–X and XII below, neutrophil is fixed to a glass matrix with alcohol, fixed neutrophil is contacted with a serum sample and a specific binding agent detectably labeled with a fluorescent compound under conditions suitable to form an immune complex comprising neutrophil, pANCA and the specific binding agent. Neutrophil is separated from any unbound serum and unbound specific binding agent. The presence of pANCA in the serum sample is then detected by the presence of a perinuclear staining pattern and the absence of pANCA in the serum sample is detected by the absence of a perinuclear staining pattern.

In accordance with preferred embodiments of the invention, however, the absence of pANCA in a serum sample using this indirect immunofluorescence format is detected as described above and the presence of pANCA in the serum sample is detected, for example as described in Examples VIII–XIII below, by further contacting second serum sample from the patient with DNase-treated neutrophil and the specific binding agent detectably labeled with the fluorescent compound under conditions suitable to form an immune complex comprising DNase-treated neutrophil, pANCA and the specific binding agent. Neutrophil is separated from any unbound serum and unbound specific binding agent. The presence of pANCA in the serum sample is then detected by the loss of the perinuclear staining pattern as compared to perinuclear staining pattern detected from the first serum sample.

In yet another embodiment of the invention, pANCA is detected in the pANCA assay using an ELISA format. As described for example in Examples VIII, IX, XIV, and XVI below, a serum sample is contacted with neutrophil and a specific binding agent detectably labeled with an enzyme under conditions suitable to form an immune complex comprising neutrophil, pANCA and specific binding agent. Neutrophil is separated from any unbound serum and unbound specific binding agent and then contacted with a suitable enzyme substrate. The presence of pANCA in the serum sample is detected by digestion of the enzyme substrate and the absence of pANCA in the serum sample is detected by absence of digestion of the enzyme substrate.

In accordance with preferred embodiments of the invention, however, the absence of pANCA in the serum sample using this ELISA format is detected as described above and the presence of pANCA in the serum sample is detected, for example as described in Examples VIII, IX and XIV–XVII below, by further contacting a second serum sample from the patient with DNase-treated neutrophil and the specific binding agent detectably labeled with an enzyme under conditions suitable to form an immune complex comprising DNase-treated neutrophil, pANCA and the specific binding agent. Neutrophil is separated from any unbound serum and unbound specific binding agent and then contacted with a suitable enzyme substrate. The presence of pANCA in the serum sample is detected by the loss of enzyme digestion as compared to enzyme digestion detected from the first serum sample.

Samples useful in the pANCA assay can be obtained from any biological fluid, for example, whole blood, plasma, or other bodily fluids or tissues having pANCA, preferably serum. When multiple samples are used in the pANCA assay, it is preferred that the same type of biological fluid or tissue is used for all samples. As used herein, the terms "patient," when referring to the origin of the sample to be assayed, means any animal capable of producing pANCA, including for example, humans, non-human primates, rabbits, rats, mice, and the like.

Neutrophil useful in the present invention can be obtained from a variety of sources, e.g., the blood of a human, non-human primates, rabbits, rats, mice, and the like, by methods known to those of skill in the art. Preferably, neutrophil employed will have specific reactivity for the species from which the sample to be tested is obtained. For example, to assay for pANCA in a sample obtained from a human patient, the neutrophil used is preferably human neutrophil.

The term "DNase-treated neutrophil" refers to neutrophil that has been treated with DNase to result in substantially complete digestion of the cellular DNA of the neutrophil. By the phrase "substantially complete digestion of cellular DNA" it is meant such digestion of the cellular DNA that the cellular DNA has substantially lost its ability to bind proteins and other cellular materials normally associated with the cellular DNA of the neutrophil. Without being bound by any particular theory, it is presently believed that at least part of the antigens of pANCA are proteins that are either intimately associated with nuclear DNA or with some aspects of nuclear structure.

Treatment of neutrophil with DNase so as to cause substantially complete digestion of cellular DNA will vary in accordance with the purity and concentration of the DNase used and include, for example, incubating the immobilized neutrophil in a concentration of DNase of about 2 to 10 units of DNase per milliliter of a suitable buffer for a time in the range of about 15 minutes to one hour at a temperature in the range of about 22° C. to 40° C.

The terms "specific binding agent for pANCA" and "specific binding agent" as used herein with regard to the pANCA assay, refer to a molecular entity capable of selectively binding pANCA or an immune complex containing pANCA which does not interfere with binding of pANCA to neutrophil. Exemplary specific binding agents useful in the pANCA assay are secondary antibody molecules (e.g., anti-Ig antibodies such as anti-IgG), complement proteins or fragments thereof, and the like which may themselves be labeled with a detectable marker. If one or more specific binding agent in the form of secondary antibody molecule is used, each secondary antibody molecule is preferably species-specific for the antibody or antigen it binds. Accordingly, in a preferred embodiment of the present invention, human blood serum is the sample and mouse anti-human IgG is the specific binding agent for pANCA. Even more preferably, a second specific binding agent is also used, preferably a goat anti-mouse secondary antibody specific for the class determining portion of the mouse anti-human IgG antibody.

Secondary antibodies useful in the practice of the present invention can be obtained by techniques well known in the art. Such antibodies can be polyclonal or preferably monoclonal. Polyclonal antibodies can be obtained, for example, by the methods in Ghose et al., *Methods of Enzymology*, Vol. 93, 326–327 (1983). For example, IgG or Fc fragments of IgG can be used as the immunogen to stimulate the production of IgG reactive polyclonal antibodies in the antisera of animals such as rabbits, goats, sheep, rodents, and the like.

Monoclonal antibodies useful in the practice of the present invention can be obtained from a number of commercially available sources. Alternatively, the antibodies can be obtained, for example, by the process described by Milstein and Kohler in *Nature*, 256:495–97 (1975) or as modified by Gerhard, *Monoclonal Antibodies*, 370–371 (Plenum Press, 1980) and discussed in greater detail above. Immunogen useful to generate secondary antibodies with specificity to pANCA include, for example, human IgG or Fc fragments of human IgG, pANCA or FAB fragments of pANCA.

Hybridomas producing secondary monoclonal antibody specific for pANCA by screening hybridoma supernates for the presence of antibody molecules that immunoreact with pANCA. Such screening methods include for example, radioimmunoassay (RIA) or enzyme linked immunosorbent assay (ELISA) using neutrophil and pANCA positive sera, for example, as immunochemical reagents.

Alternatively, monoclonal antibodies having a high affinity for pANCA can be obtained by the creation of a phage combinatorial library for pANCA and then screening for specificity by a similar process described in Barbas, C. F. et al, *Proceedings of the Nat'l Academy of Science*, 88:7978–82 (1991), incorporated herein by reference. Once the IgG fractions having greatest specificity for pANCA antigen has been isolated, anti-idiotype antibodies may be raised by methods well known in the art.

The term "pANCA-containing complex" refers to an immune complex that includes at least pANCA and will typically also include neutrophil, a specific binding agent or both.

The pANCA assays of the present invention are normally carried out at room temperature and 37° C. Because the methods involve the use of proteins, temperatures which would substantially modify the tertiary and quaternary structures of the proteins should be avoided. Accordingly, temperatures suitable for performing the pANCA assays of the present invention generally range from about 22° C. to about 38° C. The time for performing the pANCA assay steps, of course, will decrease in relation to the increase in temperature at which the methods are performed.

In still another embodiment of the present invention, any immune complex formed by contacting sample with neutrophil and specific binding agent for pANCA in the pANCA assay is separated from any uncomplexed sample and or specific binding agent prior to detecting the presence or absence of pANCA in the sample. Typically this will involve separating neutrophil subjected to the contacting step from one or more of the other reagents of that step. Methods of separating immune complex from uncomplexed material are well known in the art. When appropriate, a simple washing with a suitable buffer followed by filtration or aspiration is sufficient. If neutrophil or specific binding agent for pANCA is immobilized on a particulate support, as in the case of microparticles for example, it may be desirable to centrifuge the particulate material, followed by removal of wash liquid. If neutrophil or specific binding agent for pANCA is immobilized on membranes or filters, applying a vacuum or liquid absorbing member to the opposite side of the membrane or filter allows one to draw the wash liquid through the membrane or filter.

In a preferred embodiment of the present invention, neutrophil or specific binding agent for pANCA is immobilized on a solid matrix. The solid matrix can be any support useful in immunometric assays. However, the matrix should not significantly affect the desired activity of the neutrophil or specific binding agent for pANCA. Examples equally suitable for use in the pANCA assay are described above with regard to the VH3-15 assay.

As described herein and by methods well known to the skilled artisan, immune complexes of the pANCA assay can be directly detected, for example, by precipitation of the immune complex or indirectly detected by labeling, for example, the specific binding agent or the neutrophil with a detectable marker and detecting enzymatic conversion, radioactivity, fluorescence, color and the like. Thus in accordance with preferred embodiments of the present invention, neutrophil or, most preferably, specific binding agent for pANCA, is labeled with a detectable marker. Methods for labeling the compositions of the present invention, detectable marks suitable for use in the present invention and methods of detecting the markers and immune complexes of the present invention are discussed in detail with regard to the compositions useful in the VH3-15 assay and apply equally to the compositions useful in the pANCA assay.

The present invention also provides kits useful for screening patients for Crohn's disease and ulcerative colitis. A suitable kit includes, in an amount sufficient for at least one assay, anti-VH3-15 idiotypic antibody material, preferably the monoclonal antibody produced by the hybridoma having ATCC Accession No. HB 11720 as a separately packaged reagent. Preferably, the kits also include any one or more of the following in an amount sufficient for at least one assay: cell surface antigen, neutrophil, DNase, DNase treated neutrophil, detectable marker, enzyme substrate, VH3-15 assay control, specific binding agent for pANCA, specific binding agent for anti-VH3-15 idiotypic antibody material, anti-IgG, biotin, avidin and the like. In addition, other components such as ancillary reagents may be included, for example, stabilizers, buffers, fixatives, and the like. Cell surface antigen included in these kits can be bound to the cell membrane of *Campylobacter jejuni* cells or erythrocytes. If erythrocyte cell membrane is used, preferably it is pre-treated with bromelase or an amount of bromelase is included in the kit to pre-treat the erythrocyte cell membrane. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

The kits can be used in an "ELISA" format. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090, U.S. Pat. No. 3,850,752; and U.S. Pat. No. 4,016,043, which are all incorporated herein by reference.

Thus, anti-VH3-15 idiotypic antibody material, cell surface antigen or neutrophil, for example, can be affixed to a solid matrix to form a solid support that comprises a package in the subject diagnostic systems. A reagent is typically affixed to a solid matrix by adsorption from an aqueous medium although other modes of affixation applicable to polypeptides and nucleic acids well known to those skilled in the art can be used.

Useful solid matrices are also well known in the art. Such materials are water insoluble and include the cross-linked dextran available under the trademark from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The anti-VH3-15 idiotypic antibody material, cell surface antigen, neutrophil, labeled specific binding agent, DNase and the like of any kit described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this kit.

The packaging materials discussed herein in relation to the kits are those customarily utilized in kits and commercially available. The term "package" refers to a solid matrix or material such as glass, plastic (e.g., polyethylene, polypropylene and polycarbonate), paper, foil and the like capable of holding within fixed limits a diagnostic reagent such a protein, polypeptide fragment, antibody or monoclonal antibody of the present invention. Thus, for example, a package can be a bottle, vial, plastic and plastic-foil laminated envelope or the like container used to contain a contemplated a reagent or it can be a microtiter plate well to which microgram quantities of a contemplated reagents have been operatively affixed, i.e., linked so as to be capable of being immunologically bound by an antibody or polypeptide to be detected.

The invention will now be described in greater detail by reference to the following non-limiting examples.

EXAMPLE I

Production of Anti-VH3-15 Hybridomas

Monoclonal antibodies specific for VH3-15 polypeptides can be produced using standard hybridoma techniques, i.e., immunizing a mammal with a VH3-15 polypeptide, fusing B lymphocytes from the immunized animal with immortalized cells to produce hybridomas and then screening the hybridomas for antibodies that bind the immunogen. Representative VH3-15 polypeptides are provided in SEQ ID NO. 2 through 4. SEQ ID NO. 1 represents an example of a VH3-15 nucleic acid sequence. The germline VH3-15 nucleic acid sequence is available from Genbank. Any one or all of these polypeptides may be used as an immunogen.

Alternatively, other VH3-15 polypeptides may be created for use as immunogens from the given sequences by substitution, addition or deletion of one or more amino acids. Another alternative is to use other known VH3-15 amino acid sequence as immunogens such as, for example LJ11, LJ67. LJ23 as described in Braun, et al., *J. Clin. Invest.*, 89:1395–1402 (1992).

The nucleic acid sequence encoding LJ86 (Genbank Accession No. M82929) was subcloned into the pGEX bacterial expression system (catalog no. 27-4570-01, Pharmacia Biotech, Inc., Piscataway, N.J.) to produce a VH3-15/glutathione-S-transferase fusion protein and the fusion protein purified all in accordance with the manufacturer's instructions.

This material was then used to immunize Balb/c mice, from which hybridomas were produced and screened for IgM and IgG antibodies reacting with the VH3-15 fusion protein immunogen. More specifically, primary immunization of Balb/c mice was carried out with 10 micrograms purified VH3-15 immunogen by intrasplenic injection. See, Spitz, et al. *J. Immunol. Methods*, 70:39–43 (1984), incorporated herein by reference in its entirety. Four days later, spleen cells were harvested for fusion.

Spleenocytes from immunized animals were prepared and fused with NS-1 cell (ATCC Accession No. TIB18) as described, for example in Harlow and Lane, *Antibodies: A Laboratory Manual* (Cold Spring Harbor Laboratory 1988). Hybrids were selected by use of medium containing hypoxanthine, aminopterin and thymidine ("HAT medium") two days after fusion. Surviving hybrids were transferred to microtitre culture plates and medium supernates assessed for specific reactivity with the VH3-15 immunogen. Positive hybridomas were subcloned twice in microtitre plates and selected by ELISA for VH3-15 reactivity using peroxidase-anti-mouse Ig. (Southern Biotech Assoc., Birmingham, Ala.) Among 600 hybridomas screened, nine produced monoclonal antibodies specific for the VH3-15 immunogen. Six of these nine hybridoma cell lines are stored in liquid nitrogen by Dr. Jonathan Braun in room 4-557 of the McDonald Research Medical Laboratory located at 675 Circle Drive South Los Angeles, Calif. 90024. These six hybridoma cell lines are labeled and identified by the following laboratory names:

NS2B9D7E6F5 (and also known as BK1)

NS5A4D3F4F9 (and also known as BK2)

NS5B7F3F6E1 (and also known as BK3)

NS1H6C1D4B3 (and also known as BK4)

NS1H6B9D6 (and also known as BK5)

NS5B7F3F6E1 (and also known as BK7)

Of these, a number are IgM and IgG producing hybridomas and BK2 is an IgG.kappa producing hybridoma.

Larger amounts of monoclonal antibody were obtained by inoculating Balb/c mice interperitoneally with $1 \times 10^7$ cells per animal. Ascites protein was purified by ammonium sulphate precipitation and DEAE-Sephacel chromatography, and in some cases biotinylated with NHS-LC-biotin (Pierce, Rockford, Ill.) following manufacturer's recommendations.

EXAMPLE II

ELISA FOR SCREENING HYBRIDOMAS FOR ANTI-VH3-15 IDIOTYPIC MONOCLONAL ANTIBODY PRODUCTION

Specificity of monoclonal antibodies for VH3-15 polypeptides can be determined by a standard ELISA method described in Berberian, et al., *Science*, 261:1588–1591 (1993), incorporated herein by reference in its entirety. Briefly, ELISA plate wells were coated with various concentrations of either a known VH3-15 antibody or a known non-VH3-15 antibody. For each hybridoma being screened, monoclonal antibodies derived from the hybridoma were added to VH3-15 antibody and non-VH3-15 antibody coated wells. Specificity was detected by enzymatic digestion of substrate using peroxidase anti-mouse Ig.

More specifically, LSF2 is a human anti-*Hemophilus influenza* monoclonal antibodies encoding VH3-15 and is described in Adderson, et al., *J. Immunol.*, 147:1667–1674 (1991). In the following ELISA, LSF2 was used as an VH3-15 antibody. 477 is a human monoclonal antibody to Waldenstrom's paraproteins encoding VH3-30 and is described in Axelrod, et al., *Blood*, 77:1484–1490 (1991)). In the following ELISA, 477 was used as the non-VH3-15 antibody.

1 to 10,000 ng of VH3-15 antibody or non-VH3-15 antibody per well (or preferably 10 to 1000 ng, or even more preferably 20 ng) were diluted in 50 μL carbonate-bicarbonate buffer, pH 9.6 (Sigma, St. Louis, Mo.), added to microtiter plates (Costar, Pleasanton, Calif.), and incubated overnight at 4° C. The plates were washed 3 times for 15 minutes each with phosphate-buffered saline+0.5% Tween-20 (ELISA buffer) and blocked for 30 minutes in ELISA buffer.

Monoclonal antibodies from each hybridoma being screened were reacted against VH3-15 antibody and against non-VH3-15 antibody by adding 50 μl of monoclonal antibody (diluted 1:1000 in ELISA buffer) to sample wells and incubated for 1 hour at 4° C. Plates were washed five times with PBS-Tween 20 (0.05%) at room temperature for one minute per wash.

Monoclonal antibody specificity was detected by enzymatic digestion of substrate. Each well was incubated for one hour at 4° C. with 1:10,000 goat anti-mouse IgG horseradish peroxidase (Caltag, San Francisco, Calif.) and washed five times with PBS-Tween 20 (0.05%) at room temperature for one minute per wash.

Each well was then incubated with o-phenylenediamine dihydrochloride (Sigma) for 30 minutes at 37° C. 3N $H_2SO_4$ was added to stop the reaction. Optical density was determined by absorbance at 492 nm and ranged from 0 to 0.8 optical density units. (OD range in correspondence with 1–10,000 ng Ab used.) It is recommended that an absorbance reading two times the background be considered positive binding to antibody. Non-coated wells were used as the control. Monoclonal antibodies which bind VH3-15 antibody are considered an anti-VH3-15 idiotypic monoclonal antibody. Their specificity is confirmed by their lack of binding with non-VH3-15 antibody.

Using the foregoing assay, it can be shown that monoclonal antibodies produced in accordance with the present invention distinguish between the following VH3 gene products: VH3-30, VH3-23, and VH3-15. BK2 produced mAb which were strongly reactive with the VH3-15 antibody (LSF2), but were unreactive with non-VH3-15 antibody (477). Conversely, B6 and D12 (known anti-VH3-30 idiotypic monoclonal antibodies) were reactive with non-VH3-15 antibody (477), but unreactive with VH3-15 antibody (LSF2). 16/6 (a known anti-VH3-23 idiotypic monoclonal antibody, Young, et al., *J. Immunol.*, 145:2545–2553 (1990)) reacted with neither VH3-15 antibody (LSF2) nor non-VH3-15 antibody (477). BK2 lacked detectable reactivity with polyclonal human IgM and IgG.

These findings demonstrated that BK2 selectively bound to VH3-15 antibody (versus other closely related VH3 family gene products), and lacked reactivity with prevalent Ig sequences such as heavy or light chain constant regions. The apparent paucity of serum VH3-15 was consistent with the infrequent use of this gene, compared to other VH3 genes, in cDNA libraries prepared from polyclonal human B cell populations.

EXAMPLE III

SUBMUCOSAL STAINING OF COLONIC BIOPSY BY MONOCLONAL ANTIBODIES SPECIFIC FOR VH3-15 POLYPEPTIDES

Five colonic mucosal biopsy specimens were obtained from diagnostic colonic endoscopy specimens of patients seen at UCLA. Three of these specimens were from patients diagnosed with CD, two were from patients diagnosed with UC and one was from a normal patient without either disease. Procedures for subject recruitment, consent, and specimen procurement were in accordance with protocols approved by the Institutional Human Subject Protection Committees at UCLA and Cedars-Sinai Medical Center.

Paraffin sections of normal, UC, and CD colonic biopsies were deparaffinized and blocked for endogenous peroxidase by incubating 20 minutes in $H_2O_2$ in methanol. To rehydrate sections, slides were immersed in Coplin jars with decreasing concentrations of ethanol, and prepared for staining by washing slides in Tris-buffered saline (TBS) twice, followed by a 30 minute wash in TBS supplemented with 3% goat serum.

Anti-VH3-15 idiotypic monoclonal antibody (diluted to 1 µg/ml in TBS) was applied and incubated 2 hours at room temperature in a humidified chamber, followed by the series of washes with 200 ml TBS for 1 minute at room temperature. Sections were then incubated with 0.2 ml goat anti-mouse Ig peroxidase (Caltag) for 30 minutes at room temperature and then washed with TBS as described above. Finally, binding of anti-VH3-15 idiotypic monoclonal antibody was visualized by the production of a brown precipitate using 3-amino-9-ethylcarbazole (Sigma) substrate. Control slides were stained in the same fashion with the substitution of an isotype-matched mouse IgG. The anti-VH3-15 idiotypic monoclonal bound to intravascular erythrocytes in biopsies from UC patients and CD patients but not in normals.

EXAMPLE IV

FLOW CYTOMETRIC ASSAY FOR VH3-15 AUTOANTIBODIES

Blood serum samples from normal, UC, CD, and other acute and chronic enterocolitis patients were assayed by flow cytometry to detect and quantify VH3-15 autoantibody activity. Samples were obtained from 101 subjects among patients seen at the Inflammatory Bowel Disease and Gastroenterology clinics of UCLA Center for Health Sciences and Cedars-Sinai Medical Center. These samples were segregated into disease groups, as set forth in Table 3 below, by standard clinical criteria.

TABLE 3

Numbers of subjects studied for serum VH3-15 autoantibody by flow cytometry.

| | |
|---|---|
| Non-transfused healthy adults | 17 |
| Ulcerative colitis | 22 |
| Post-Colectomy UC | 7 |
| Crohn's disease | 17 |
| Other colitis | 38 |
| Campylobacter enterocolitis | 10 |
| Collagenous colitis | 8 |
| Acute infectious colitis | 3 |
| Shigella colitis | 1 |
| Acute self-limited diarrhea | 2 |
| Pseudomembranous colitis | 5 |
| Acute schistosomiasis | 2 |
| Amoebic colitis | 2 |
| Eosinophilic diarrhea | 1 |
| Neutropenic colitis | 1 |
| Irritable bowel syndrome diarrhea | 1 |
| Radiation proctitis | 1 |
| Laxative abuse | 1 |
| Total | 101 |

A. VH3-15 Autoantibody Associated With CD and UC Confirmed As Encoding VH3-15 Polypeptide $1 \times 10^6$ O$^{negative}$, Rh$^{negative}$ blood bank reagent red blood cells (Dade, Miami, Fla.) in 100 µl physiological saline were incubated with 100 µl of UC and CD serum samples at room temperature for 30 minutes. The cells were washed in flow buffer (Hanks balanced salt solution, 2% fetal calf serum, and 10 mM HEPES, pH 7.4). After washing, 50 µl cell aliquots in flow buffer were incubated on ice for 30 minutes with 0.5 µg of a biotinylated anti-VH3-15, anti-VH3-23 or anti-VH3-30 idiotypic monoclonal antibody (BK2, 16/6 and D12 or B6, respectively). The cells were washed with flow buffer, incubated on ice for another 30 minutes with 5 µl of streptavidin-phycoerythrin (Becton-Dickinson, Burlingham, Calif.), and finally washed again with flow buffer. Fluorescence was detected by cytofluorography using a Becton-Dickinson FACSCAN™ instrument. Histograms of log fluorescence were generated and analyzed by Lysis II™ software.

UC and CD samples incubated with anti-VH3-23 or anti-VH3-30 idiotypic monoclonal antibodies exhibited a fluorescent intensity and pattern equivalent to that of the control (serum and streptavidin-phycoerythrin alone). However, UC and CD samples incubated with anti-VH3-15 idiotypic monoclonal antibody exhibited a uniform shift in fluorescent intensity and pattern to one 4-fold brighter than the control.

The marked increase in fluorescent intensity demonstrated by the anti-VH3-15 idiotypic antibody in UC and CD samples indicates that the VH3-15 autoantibody encodes a VH3-15 polypeptide, but not a VH3-23 or VH3-30 polypeptide. This distinction is notable, since B cells expressing the latter two gene subfamilies are actually much more prevalent than VH3-15 expressing B cells.

The uniform fluorescent pattern seen in UC and CD samples indicates that the VH3-15 autoantibody recognizes a common red blood cell antigen. Reagent red cells varying in minor blood group antigens did not differ in reactivity with the VH3-15 autoantibody. This indicated that the autoantigen could not be correlated with a conventionally-defined blood group antigen.

B. VH3-15 Autoantibody Levels Are Elevated In UC and CD

Blood serum samples from normal, UC and CD patients were assayed by flow cytometry (as described in Example IVA above) to detect, quantify and compare VH3-15 autoantibody levels. For numerical comparison between samples, values for relative fluorescence intensity were calculated: (fluorescence with serum, anti-VH3-15 idiotypic monoclonal antibody, and phycoerythrin)/ (mean fluorescence with anti-VH3-15 idiotypic monoclonal antibody and phycoerythrin). Relative fluorescence intensity values for each sample are given in FIG. 1. Mean values for subjects in each disease group are depicted by a black bar. Levels of VH3-15 autoantibody were significantly elevated in CD patients (mean group value of 8.5) and UC patients (mean group value 6) as compared to healthy normal patients (mean group value 2.5).

C. VH3-15 Autoantibody Is Unique to UC, CD and *C. jejuni*

Two other patient groups were tested to confirm that elevated VH3-15 autoantibody levels were specific to patients with UC and CD, and were not elicited as part of general response to mucosal injury. First, blood serum samples from seven UC patients who had previously undergone colectomy (between six months and three years earlier) were tested for VH3-15 autoantibody levels. For numerical comparison between samples, values for relative fluorescence intensity were calculated: (fluorescence with serum, anti-VH3-15 idiotypic monoclonal antibody, and phycoerythrin)/(mean fluorescence with anti-VH3-15 idiotypic monoclonal antibody and phycoerythrin). Relative fluorescence intensity values for each sample are given in FIG. 1. Mean values for subjects in each disease group is depicted by a black bar. Although the mean level of the post-colectomy UC subgroup (3.8) was apparently reduced compared to pre-colectomy UC patients (6), VH3-15 autoantibody levels were still significantly elevated above healthy normal controls (2.5).

The second patient group tested were patients with other acute or chronic colitis. Of the sera tested, 32/38 had VH3-15 autoantibody levels comparable to normals. An interesting and unexpected finding was that the 6 sera with elevated VH3-15 autoantibody levels (mean group value of 5) corresponded to the group of patients with *Campylobacter jejuni* enterocolitis. The association of these three disparate gastrointestinal diseases with VH3-15 autoantibody is unexpected.

The VH3-15 autoantibody is selectively expressed among individuals with CD, UC and *Campylobacter jejuni* enterocolitis. Thus, detection of VH3-15 autoantibody levels above the upper 90% confidence limit for normals (relative fluorescence>3.25) is a sensitive indicator of these diseases: Crohn's disease (17/17, 100%), ulcerative colitis (26/29, 90%), and *C. jejuni* enterocolitis (7/10, 70%). In this range, the detection of VH3-15 autoantibody is also specific for this subset (50/53, 94%), since positive sera were detected in only 3/28 (11%) of individuals with other gastrointestinal diseases.

EXAMPLE V

Immunoprecipitation of Erythrocyte Membrane Cell Surface Antigen

Immunoprecipitation was used to isolate the erythrocyte proteins recognized by VH3-15 autoantibody. To focus analysis on the surface-exposed antigens accounting for the flow cytometry findings, detection was restricted to surface-displayed proteins in two ways: erythrocytes were chemically surface-labeled, and sera were reacted with intact erythrocytes prior to cell lysis.

Surface-exposed erythrocyte membrane proteins were first labeled by surface biotinylation. Intact $O^{negative}$, $Rh^{negative}$ blood bank reagent red blood cells (Dade-Baxter, Miami, Fla.) were pre-treated with bromelase (Dade-Baxter, Miami, Fla.) following manufacturer's instructions and then washed in PBS three times, resuspended at 1% ($1 \times 10^8$ cells/ml) in PBS with 50 µg/ml NHS-LC-biotin (Pierce), and rotated for 15 minutes at room temperature. Biotinylated cells were then washed with PBS, and aliquots ($3 \times 10^6$ cells in PBS) were combined with 300 µl test serum. Test sera were selected from 11 healthy controls and 9 patients (5 CD and 4 UC patients) to represent a range of VH3-15 autoantibody levels identified above by flow cytometry. The biotinylated cell/test serum were rotated for 1 hour at room temperature.

Cells were again washed with PBS, incubated with 1.5 µg anti-VH3-15 idiotypic monoclonal antibody for 30 minutes at 4° C., and washed with PBS again. The cells were then treated with 100 µl lysis buffer (2% Triton-X in PBS) for one hour on ice. Lysates were then diluted with 0.9 ml PBS and incubated with 20 µL goat anti-mouse IgG(H+L) sepharose beads (Zymed, San Francisco, Calif.) for 30 minutes on ice. Beads were washed three times with PBS, and eluted by 5 minutes at 100° C. with 50 µl Laemmli sample buffer including 5% 2-mercaptoethanol.

Sample aliquots (10 µl) were run on 12.6% SDS-PAGE gels as described in Cleveland et al., *J. Biol. Chem.* 252:1102 (1977) incorporated herein by reference, and electro-transferred to nitrocellulose filters following standard procedures. See, Towbin, et al., *Proc. Natl. Acad. Sci. USA*, 76:4350 (1979), incorporated herein by reference. To detect the surface-labeled immunoprecipitated proteins, the blots were stained with streptavidin-peroxidase (diluted 1:5000) and visualized by enhanced chemiluminescence (ECL) (Amersham, Chicago, Ill.) following the supplier's recommendations. Lanes stained either in the absence of serum or with an anti-VH3-15 idiotypic monoclonal antibody matched isotype control immunoglobulin were controls for nonspecific binding.

Two protein species (22 and 28 kD) were detected by positive sera (sera which produced any detectable proteins after immunoprecipitation) and the same pattern was observed for sera from 9/9 patients with UC or CD. In contrast, no surface proteins were detected by sera from 11/11 healthy subjects. No detectable non-specific bands were observed with immunoprecipitations in the absence of serum or anti-VH3-15 idiotypic monoclonal antibody. It was also determined that the autoantigen does not correspond to commonly analyzed blood group antigens, since the different typing panel red cell samples were all autoantigen positive.

Thus, VH3-15 autoantibody from different individuals shared a common protein antigen specificity. The autoantigen is surface-exposed on the erythrocyte, and is at least in part protein-expressed, since immunoprecipitation of surface-labeled erythrocytes with positive sera detected the same pair of protein species (22 and 28 kD).

EXAMPLE VI

Fixed Erythrocyte ELISA

An alternative method for detecting and quantifying serum VH3-15 autoantibody was also designed. $1 \times 10^6$ O negative, Rh negative blood bank reagent red blood cells (Dade-Baxter, Miami, Fla.) were prepared for bromelase digestion by spinning them down at 1500 RPM for 10 minutes at room temperature and then washing them twice with saline 0.9% at 1500 RPM for 10 minutes. Cells were digested with Bromelase Enzyme Reagent (Dade-Baxter, Miami, Fla.) in accordance with the manufacture's directions (normally 1 ml of bromelase per $1 \times 10^6$ red blood cells). Then the cells were washed twice with saline 0.9% at 1500 RPM for 10 minutes.

The red blood cells were then lysed and cell membrane purified as follows:

1. The total volume of RBC pellet was divided into four microfuge tubes (~50 µl each) after the last saline wash.
2. Eight times the pellet volume of 60 mOsm buffer made from stock solution buffer containing 0.200 m NaCl, 0.075 m$Na_2HPO_4$, and 0.025 m$KH_2PO_4$ was added.
3. The microfuge tubes were shaken for 30 minutes at 30° C.
4. The tubes were centrifuged at 10,000×g for 20 minutes.
5. The supernatant very carefully aspirated.
6. Steps 2, 3 and 4 were performed with 30 and 20 mOsm.
7. The protein on the ghost was measured by Lowry protein quantitation assay (Biorad, Richmond, Calif.) using a protein standard (e.g. bovine serum albumin).
8. Cells may be stored at −70° C. for up to about 1 week.

An ELISA was performed using the purified erythrocyte cell membrane described above:

1. EIA/RIA Plate form costar (Sigma) were coated with 200 ng erythrocyte cell membrane in 50 µl of 0.05M sodium carbonate buffer, pH 9.6 per well using the instructions of SIGMA.

2. Coated plates were incubated over night at 4° C.
3. Coated wells were washed three times with Tween-PBS.
4. 50 µl of serum from normals, CD patients or UC patients diluted with Tween-PBS to a preferred concentration of 1/2500 was added per well. (Alternative concentrations useful in the present assay include, for example 1/1000, 1/2000, 1/5000 and 1/10,000).
5. Plates were incubate for 1 hour at room temperature.
6. Wells were washed three times with Tween-PBS.
7. 50 µl of anti-VH3-15 idiotypic monoclonal antibody was added per well at 1/1000 dilution.
8. Plates were incubated for 1 hour at room temperature.
9. Wells were washed twice with Tween-PBS.
10. 50 µl goat anti-mouse IgG was added per well at 1000 dilution.
11. Plates were incubated for 1 hour at room temperature.
12. Wells were washed three times with Tween-PBS.
13. An OPD tablet (Sigma) was diluted in OPD buffer following instructions from SIGMA and 50 µl was added per well.
14. The plates were incubated at 37° C. for 20 minutes.
15. The reaction was stopped using 50 µl of 3N $H_2SO_4$.
16. Absorbencies were determined by a microtiter plate ELISA reader at 492 nm for twenty seven normal, CD and UC samples each and are provided in Table 4.

TABLE 4

Mean absorbancies corrected for background, standard error of mean and p values, as compared to normal group for reported absorbancies at 492 nm of serum samples tested for VH3-15 autoantibody by fixed erythrocyte ELISA.

|  | Normal | CD | UC |
|---|---|---|---|
| MEAN | 0.035 | 0.088 | 0.056 |
| SEM | 0.007 | 0.016 | 0.013 |
| P VALUE | — | 0.004 | 0.15 |
| Sample |  |  |  |
| 1 | 0.120 | 0.160 | 0.066 |
| 2 | 0.040 | 0.119 | 0.012 |
| 3 | 0.011 | 0.256 | 0.056 |
| 4 | 0.032 | 0.066 | 0.140 |
| 5 | 0.021 | 0.030 | 0.076 |
| 6 | 0.011 | 0.010 | 0.056 |
| 7 | 0.005 | 0.036 | 0.003 |
| 8 | 0.016 | 0.015 | 0.025 |
| 9 | 0.016 | 0.258 | 0.019 |
| 10 | 0.014 | 0.311 | 0.002 |
| 11 | 0.006 | 0.012 | 0.326 |
| 12 | 0.005 | 0.057 | 0.008 |
| 13 | 0.001 | 0.010 | 0.012 |
| 14 | 0.001 | 0.012 | 0.021 |
| 15 | 0.023 | 0.077 | 0.041 |
| 16 | 0.072 | 0.006 | 0.013 |
| 17 | 0.002 | 0.146 | 0.012 |
| 18 | 0.016 | 0.123 | 0.047 |
| 19 | 0.125 | 0.079 | 0.087 |
| 20 | 0.000 | 0.056 | 0.071 |
| 21 | 0.032 | 0.058 | 0.097 |
| 22 | 0.042 | 0.047 | 0.018 |
| 23 | 0.088 | 0.058 | 0.063 |
| 24 | 0.083 | 0.100 | 0.089 |
| 25 | 0.052 | 0.084 | 0.098 |
| 26 | 0.012 | 0.088 | 0.026 |
| 27 | 0.089 |  | 0.016 |

TABLE 5

Number of positive and negative samples by disease group using fixed erythrocyte ELISA tested for VH3-15 autoantibody. Positive sample is a sample having an amount of VH3-15 autoantibody that exceeds control.

| DISEASE GROUP | # POSITIVE | # NEGATIVE |
|---|---|---|
| NORMAL | 9 | 18 |
| UC | 15 | 12 |
| CD | 19 | 8 |

TABLE 6

Number of positive and negative samples by disease group using fixed erythrocyte ELISA tested for VH3-15 autoantibody. Positive sample is a sample that exceeds control by at least one SEM for control providing 85% confidence.

| DISEASE GROUP | # POSITIVE | # NEGATIVE |
|---|---|---|
| NORMAL | 7 | 20 |
| UC | 13 | 14 |
| CD | 18 | 9 |

The titre of VH3-15 autoantibody was also quantified in antibody units. An antibody unit is the percent of the absorbance ratio (test serum/positive reference serum) of samples at 1:2500 read at 492 nm. The positive test serum was a high titre CD sample having an absorbance of 0.392 after subtracting the background, in which coated wells were reacted with reagents but no serum. A reading of seventy-five (75) antibody units or greater (2.5 times the mean antibody units for normals) was considered positive for IBD with 90% confidence limits. The mean antibody units for normal samples was 29±6 (standard error of mean, "SEM"). The mean antibody units for UC was 54±18 (SEM). The mean antibody unit for CD was 164±20 (SEM). The results of the assay performed on 27 samples each for UC, CD and healthy normal patients are reported in Table 6.

TABLE 7

Number of positive and negative samples by disease group using fixed erythrocyte ELISA tested for VH3-15 autoantibody. Positive sample is a sample that has seventy-five (75) antibody units or greater (2.5 times the mean antibody units for normals) providing 90% confidence limits.

| DISEASE GROUP | # POSITIVE | # NEGATIVE |
|---|---|---|
| NORMAL | 2 | 25 |
| UC | 9 | 18 |
| CD | 23 | 4 |

EXAMPLE VII

Fixed *Campylobacter jejuni* ELISA

As an alternative to the ELISA of Example VI, an ELISA using fixed *Campylobacter jejuni* cells was also developed.

1. EIA/RIA Plate form costar (Sigma) were coated with $5 \times 10^4$ *Campylobacter jejuni* (ATCC Accession No. 29428) in 50 µl 0.05M sodium carbonate buffer, pH 9.6 per well following the procedure described in Horwitz, M. A. and Schlesinger, L. S., *Infection Immunity*, 62: 280–289 (1994), incorporated herein by reference. Alternatively wells may be coated with bacteria in the range of about $5 \times 10^2$ to about $5 \times 10^5$.

2. Coated plates were incubated overnight at 4° C.
3. Coated wells were washed three times with Tween-PBS.
4. 50 µl of serum diluted with Tween-BPS to a preferred concentration of 0.01% was added per well. (Alternative concentrations useful in the present assay range from about 0.1% to about 0.0001%.)
5. Plates were incubate for 1 hour at room temperature.
6. Wells were washed three times with Tween-PBS.
7. 50 µl of anti-VH3-15 idiotypic monoclonal antibody was added per well at 1/1000 dilution.
8. Plates were incubated for 1 hour at room temperature.
9. Wells were washed twice with Tween-PBS.
10. 50 µl goat anti-mouse IgG was added per well at 1/1000 dilution.
11. Plates were incubated for 1 hour at room temperature.
12. Wells were washed three times with Tween-PBS.
13. An OPD tablet (Sigma) was diluted in OPD buffer following instructions from SIGMA and 50 µl was added per well.
14. The plates were incubated at 37° C. for 20 minutes.
15. The reaction was stopped using 50 µl of 3N $H_2SO_4$.
16. Absorbencies were determined by a microtiter plate ELISA reader at 492 nm.

Optical density readings are for two serum samples from patients diagnosed Crohn's disease, two serum samples from patients diagnosed with ulcerative colitis and one sample from a normal patient are provided in FIG. 2. Once again, high titre VH3-15 autoantibody was detected in IBD patients as compared to normals. In this assay, VH3-15 autoantibody concentrations exceed normals by up to about eight times.

EXAMPLE VIII

Separation of human Peripheral Blood Lymphocytes by Ficoll-Hypaque Gradient Centrifugation 1. Add 31.8 g Ficoll 400 (Pharmacia, Sweden) to 400 ml deionized $H_2O$ in a 500 ml bottle. Shake vigorously until dissolved. Add 100 ml of 50% sodium diatrizoate hypaque (UCLA Pharmacy, Los Angeles, Calif.) and mix.
2. Check specific gravity using a hydrometer. It should be 1.077–1.080.
3. Filter-sterilize Ficoll-hypaque solution through a 0.22 or 0.45 µl bottle top filter. The Ficoll-hypaque solution may be stored at 4° C., protected from light.
4. Pour 15 ml Ficoll-hypaque solution into a 50 ml conical centrifuge tube. Carefully overlayer 30 ml heparinized blood.
5. Centrifuge at 1000×g (2000 RPM) for 20 min.
6. Remove interface using a serologic pipet or pasteur pipet and place into 50 ml conical centrifuge tube.
7. Dilute interface layer with at least an equal volume of Hanks' Balanced Salt Solution (HBSS) (Irvine Scientific, Santa Ana, Calif.).
8. Centrifuge at 400×g (1200 RPM) for 5 min.
9. Decant supernatant, resuspend pellet, and add 50 ml HBSS.
10. Repeat twice steps 8 and 9.
11. Resuspend cells in RPMI 1640 (Irvine Scientific, Santa Ana, Calif.)+5% fetal calf serum (GIBCO, Gathersberg, Md.).

EXAMPLE IX

Isolation of Neutrophil

1. Using a pipet, carefully remove serum and remaining Ficoll-Hypaque from red blood cell pellet resulting from procedure described in Example VIII.
2. Add 10 ml 6% dextran to 15 milliliters of pellet.
3. Top off with 1× HBSS to 50 ml. Re-suspend pellet.
4. Allow red blood cells to settle, approximately 45 minutes to one hour.
5. Separate supernatant, discard pellet. Top supernatant off with 1× HBSS to 50 ml and centrifuge for 5 minutes at 1800 rpm.
6. Decant supernatant and tap pellet. Hypotonically lyse remaining red blood cells by adding 9 ml deionized water, swirl, and then add 1 ml 10× HBSS and immediately dilute with 1× HBSS to 50 ml.
7. Centrifuge for 5 minutes at 1000 rpm. Discard supernatant and re-suspend pellet in 15 ml 1× HBSS.

EXAMPLE X

Immobilization of Neutrophil on Glass Slides

1. Count cells in suspension of step 7 of Example IX using a microscope and hemacytometer and resuspend cells in sufficient volume of 1× HBSS to achieve $2.5 \times 10^6$ cells per ml.
2. Use Cytospin 3™ (Shandon, Inc. Pittsburgh, Pa.) at 500 rpm for 5 minutes to apply 0.01 ml of the re-suspended cells to each slide.
3. Fix cells to slide by incubating slides for 10 minutes in sufficient volume of 100% methanol to cover sample. Allow to air dry. The slides may be stored at −20° C.

EXAMPLE XI

DNase Treatment of Neutrophil Immobilized on Glass Slide

Prepare a DNase solution by combining 3 units of Promega RQ1™ DNase per ml buffer containing 40 mM of TRIS-HCl (pH 7.9), 10 mM of sodium chloride, 6 mM magnesium chloride and 10 mM calcium chloride. Promega RQ1™ DNase can be obtained from Promega, of Madison, Wis.

Rinse slides prepared in accordance with Example III with about 100 ml phosphate buffered saline (pH 7.0–7.4) for 5 minutes. Incubate immobilized neutrophils in 0.05 ml of DNase solution per slide for about 30 minutes at 37° C. Wash the slides three times with about 100–250 ml phosphate buffered saline at room temperature.

EXAMPLE XII

Immunofluorescence Assay

1. Add 0.05 ml of a 1:20 dilution of human sera in phosphate buffered saline to slides treated with DNase in accordance with Example XI and to untreated slides of Example X. Add 0.05 ml phosphate buffered saline to clean slides as blanks. Incubate for 0.5 to 1.0 hours at room temperature in sufficient humidity to minimize volume loss.
2. Rinse off sera by dipping into a container having 100–250 ml phosphate buffered saline. Soak slide in phosphate buffered saline for 5 minutes. Blot lightly.

3. Add 0.05 ml goat F(ab')$_2$ anti-human IgG(μ)-FITC, at a 1:1000 antibody:phosphate buffered saline dilution, to each slide. Incubate for 30 minutes at room temperature, in sufficient humidity to minimize volume loss. (Goat F(ab')$_2$ anti-human IgG( )-FITC is available from Tago Immunologicals, Burlingame, Calif., catalogue #4200.)

4. Rinse off antibody with 100–250 ml phosphate buffered saline. Soak slides for 5 minutes in 100–250 ml phosphate buffered saline, then allow to air dry.

5. Read fluorescence pattern on fluorescence microscope at 40×.

If desired, any DNA can be stained with propidium iodide stain by rinsing slides well with phosphate buffered saline at room temperature and stain for 10 seconds at room temperature. Wash slide three times with 100–250 ml phosphate buffered saline at room temperature and mount cover slip.

EXAMPLE XIII

DNase Sensitivity of pANCA Specific Antigen Using Immunofluorescence Assay

DNase obtained from Promega was used at a working concentration of 3 units/ml. DNase concentration was optimized by titrating the amount of DNase added (from 1 to 10 units/ml) and examining the extent of DNA digestion by propidium iodide staining and/or reaction with anti-DNA antisera. Digestion of cytocentrifuged, methanol fixed neutrophils was carried out at 37° C. for 30 minutes with DNase solubilized in 40 mM Tris-HCl (pH 7.9) buffer containing 10 mM NaCl, 6 mM MgCl$_2$ and 10 mM CaCl$_2$. Virtually all cellular DNA was lost, as indicated by the lack of propidium iodide staining. Also lost was the reaction of an anti-histone positive serum. DNase reaction carried out as described herein does not significantly alter nuclear or cellular morphology.

Neutrophils treated with trypsin at various concentrations no longer reacted with UC pANCA positive sera nor with anti-histone positive serum, indicating that at least part of the pANCA reactive antigen is a protein. Similarly, pepsin digestion of neutrophils abolished PSC pANCA positive serum reaction, again indicating the proteinaceous character of this antigenic species.

Panels of UC pANCA positive and c-ANCA positive patient sera were examined for DNase sensitivity using cytocentrifuged, methanol fixed slides as described above. Two other types of reactions were noted. Some pANCA positive sera lost the perinuclear aspect of the reaction and became cytoplasmic after DNase treatment, while c-ANCA positive sera generally remained cytoplasmic. Additionally, some sera that were found to have both a perinuclear and cytoplasmic ANCA staining reaction always lost the perinuclear aspect of the reaction after DNase treatment of neutrophils. These DNase-induced staining patterns proved to be highly reproducible from experiment to experiment.

These data indicate at least three ANCA reactions are possible in response to DNase treatment of immobilized neutrophils; 1) a pANCA reaction that is abolished, 2) a pANCA reaction that becomes cytoplasmic and 3) a c-ANCA reaction that persists. In all of these cases, the DNase digestion was complete as evidenced by a lack of propidium iodide staining as well as lack of reaction by anti-DNA antibody. Finally, it was also examined whether prior reaction of neutrophils with pANCA positive serum would effect the DNase sensitivity of antigen. The perinuclear reaction is maintained even after DNase digestion when neutrophils are first treated with the pANCA positive serum. This result indicates a protective effect of antibody binding against either physical loss of antigen or loss of epitope recognition.

EXAMPLE XIV

Immobilization of Neutrophil on Microtiter Plate

1. Count cells in suspension of step 7 of Example IX using a microscope and hemacytometer and re-suspend cells in sufficient volume of 1× HBSS to achieve 2.5×10$^6$ cells per ml. Add 0.1 ml per well to a 96-well microtiter Immulon 1™ or Immulon™ plate (available from Dynatech Laboratories of Chantilly, Va.) and let settle for 30–60 minutes.

2. Pull supernatant with 8 channel manifold connected to a vacuum and let plate air dry (approximately 2 hours) or turn upside down on the grate of a laminar flow hood to dry (approximately 10 minutes).

3. Fix cells to well by incubating cells for 10 minutes in 0.1 ml of 100% methanol per well. Discard methanol and let plate air dry. Store at −20° C.

EXAMPLE XV

DNase Treatment of Neutrophil Immobilized on Microtiter Plate

A DNase solution is prepared by combining 3 units of promega RQ1™ DNase per ml buffer containing 40 mM of Tris-HCl (pH 7.9), 10 mM sodium chloride, 6 mM magnesium chloride and 10 mM calcium chloride.

Rinse plates prepared in accordance with Example XIV once with 25 ml phosphate buffered saline. Incubate immobilized neutrophils in 0.1 ml of DNase solution per well for about 30 minutes at 37° C. Wash the wells three times with a total of about 100 ml phosphate buffered saline. Block the wells by adding 0.15 ml of 0.25% bovine serum albumin in phosphate buffered saline (pH 7.4) and allowing to stand at room temperature for about one hour. Discard blocking fluid.

EXAMPLE XVI

DNase-Treated, Fixed Neutrophil ELISA

1. Add 0.1 ml human sera diluted as desired with phosphate buffered saline containing 0.25% bovine serum albumin to each well of the microtiter plates prepared in accordance with Example XV and Example XIV (i.e., with and without the DNase treatment). Add 0.01 ml phosphate buffered serum containing 0.25% bovine serum albumin to blank wells. Let stand at room temperature for one hour, in sufficient humidity to minimize volume loss.

2. Aspirate serum. Wash three times with a total of about 100 ml phosphate buffered saline containing 0.02% sodium azide (NaN$_3$) and 0.05% Tween.

3. Add to each well 0.1 ml of a 1:1000 dilution of alkaline phosphatase-coupled goat anti-human IgG antibody in phosphate buffered saline containing 0.25% bovine serum albumin. Goat F(ab')$_2$ anti-human IgG(Fc)-alkaline phosphatase may be obtained from Jackson Immuno-Research Laboratories in West Grove, Pa. Incubate for one hour at room temperature in sufficient humidity to minimize volume loss.

4. Wash three times with a total of 100 ml phosphate buffered saline containing 0.02% sodium azide (NaN$_3$) and 0.05% Tween. Wash three more times with TRIS-NaCl solution containing 0.05M Tris, 0.15M NaCl, and 0.02% sodium azide, pH 7.5.
5. Combine 0.75 g disodium p-nitrophenol phosphate (United States Biochemicals catalogue #19587 or AMRESCO catalogue #P0364) with a Tris buffer containing 75 mM Tris-HCl, 1.5 mM MgCl$_2$, 0.02% sodium azide, pH 8.6 to form a substrate containing solution. Add 0.01 ml substrate containing solution to each well. Incubate at room temperature for 60 to 90 minutes in sufficient humidity to minimize volume loss, until blank wells reach 0.8 in absorbance.
6. Read plate at 405 nm in an EMAX Microplate Reader (Molecular Devices, Menlo Park, Calif.)

EXAMPLE XVII

Change in ANCA Binding to DNase Treated Neutrophils Relative to Control Untreated Cells using DNase-Treated Fixed Neutrophil ELISA In a panel of p-ANCA positive UC sera, the subset found to lose greater than 50% of ANCA binding by ELISA corresponds to those that lost most or all of the p-ANCA staining by immunofluorescent staining. On the other hand, sera showing less than about 50% reduction in ANCA binding by ELISA were found to display a p-ANCA pattern that converted to cytoplasmic staining after DNase digestion of neutrophils. In this latter group was also found a few sera with a mixture of perinuclear/cytoplasmic staining pattern that retained only the cytoplasmic pattern post DNase treatment. The one serum displaying a cytoplasmic ANCA staining pattern was found to have increased ANCA binding post DNase treatment. The majority (4 out of 6) of pANCA positive PSC sera lost less than 50% of the ANCA binding after DNase treatment of neutrophils; in contrast only 5 out of 14 UC p-ANCA positive sera showed such a loss. By immunofluorescent staining these PSC sera were found to display a pANCA staining pattern that became cytoplasmic after DNase treatment.

Thus, the DNase-treated, fixed neutrophil ELISA may be used to distinguish UC and PSC from CD, as well as other types of inflammatory conditions of the intestines. The unique perinuclear/cytoplasmic staining patterns associated with immunofluorescent-type assays confirms the reliability of ELISA assay and may allow further distinctions between UC and PSC.

EXAMPLE XVIII

ANCA in Pediatric UC

In the pediatric population, distinguishing between UC, Crohn's disease (CD) and allergic colitis in children with rectal bleeding (RB) is particularly difficult. Since the occurrence of ANCA in adult patients with UC has been well established, studies were undertaken to determine the relationship between the occurrence of ANCA and pediatric UC. To determine whether the presence of ANCA, as measured by DNase-treated fixed-neutrophil ELISA is sensitive and specific for pediatric UC, serum from children with UC (mean age=13), CD (mean age=14), RB (mean age=3) and other gastrointestinal inflammatory disorders (mean age=8) were tested in a blinded fashion. All ELISA positive samples were examined using immunofluorescence assay described above to determine ANCA staining patterns. ANCA was expressed as a percentage of UC positive sera binding and defined as positive when the value exceeded 2 standard deviations above the mean for normal control sera (>)12%. The results are presented in Table 8.

TABLE 8

| ANCA in pediatric UC. | | | | | | |
|---|---|---|---|---|---|---|
| | Number of Patients | Number of ANCA+ (%) | MEAN % Positive Cont. | | MEAN Reciprocal Titer | |
| | | | Total | ANCA+ | Total | ANCA+ |
| UC | 29 | 21 (72) | 44 | 57 | 527 | 705 |
| CD | 41 | 7 (17) | 8 | 16 | 61 | 114 |
| RB | 13 | 3 (23) | 8 | 17 | 87 | 208 |
| Non-IBD | 94 | 7 (7) | 6 | 21 | 63 | 229 |

UC = ulcerative colitis
CD = Crohn's disease
RB = rectal bleeding

Seventy-two percent of children with UC were ANCA positive compared to 17% with CD, 23% with RB and 7% with other gastrointestinal inflammatory disorders (Table 8). The mean percent of positive control at 1:100 dilution was also significantly higher in UC ($p<0.00$ vs CD and non-IBD, $p<0.01$ vs RB). In addition, mean titers of ANCA positive samples were significantly higher, making ELISA titer very specific for UC. The presence of a perinuclear immunofluorescence pattern correlated with titer. It is therefore seen that ANCA is sensitive (72%) and specific (89%) for UC versus other inflammatory disorders.

Although the invention has been described with reference to presently preferred embodiments, it should be understood that various modifications can be made without departing from the spirit of the invention.

---

We claim:

1. A method of screening a patient for Crohn's disease ("CD") and ulcerative colitis ("UC"), comprising:
   (a) determining the amount of VH3-15 autoantibody in a sample from the patient,
   (b) detecting the presence or absence of pANCA in a sample from the same patient,
   wherein an amount of VH3-15 autoantibody in the sample which exceeds the amount of VH3-15 autoantibody in a VH3-15 assay control and the absence of pANCA indicates CD, and
   wherein an amount of VH3-15 autoantibody in the sample that does not exceed the amount of VH3-15 autoantibody in a VH3-15 assay control and the presence of pANCA indicates UC.

2. The method of claim 1, wherein determining the amount of VH3-15 autoantibody in a sample comprises contacting the sample with anti-VH3-15 idiotypic antibody material under conditions suitable to form a VH3-15 autoantibody-containing immune complex and detecting the amount of immune complex.

3. The method of claim 2, wherein the sample comprises a colonic biopsy.

4. The method of claim 1, wherein determining the amount of VH3-15 autoantibody in a sample comprises contacting the sample with cell surface antigen and anti-VH3-15 idiotypic antibody material under conditions suitable to form a VH3-15 autoantibody-containing immune complex and detecting the amount of VH3-15 autoantibody-containing immune complex.

5. The method of claim 4, wherein the sample comprises human blood serum.

6. The method of claim 4 wherein the cell surface antigen is bound to the surface of Campylobacter jejuni cell membrane.

7. The method of claim 4 wherein the cell surface antigen is bound to the surface of human erythrocyte cell membrane.

8. The method of claim 7, wherein the human erythrocyte cell membrane has been pre-treated with bromelase.

9. The method of claim 8, wherein the erythrocyte cell membrane is immobilized.

10. The method of claim 4, wherein the anti-VH3-15 idiotypic antibody material is labeled with a detectable marker.

11. The method of claim 10, wherein the anti-VH3-15 idiotypic antibody material comprises antibody material produced by a hybridoma having ATCC Accession No. HB 11720.

12. The method of claim 11, wherein detecting the amount of VH3-15 autoantibody-containing immune complex comprises detecting the amount of complexed anti-VH3-15 idiotypic antibody material.

13. The method of claim 12, wherein the amount of complexed anti-VH3-15 idiotypic antibody material is detected by detecting enzymatic conversion, radioactivity, fluorescence or color.

14. The method of claim 13, wherein the cell surface antigen and the anti-VH3-15 idiotypic antibody material are sequentially contacted with the sample.

15. The method of claim 13, wherein the cell surface antigen and the anti-VH3-15 idiotypic antibody material are simultaneously contacted with the sample.

16. The method of claim 1, wherein detecting the presence or absence of pANCA in a sample comprises contacting the sample with neutrophil and a specific binding agent for pANCA under conditions suitable to form a pANCA-containing immune complex and detecting the presence or absence of pANCA-containing immune complex, wherein the presence of pANCA-containing immune complex indicates the presence of pANCA in the sample and the absence of pANCA-containing immune complex indicates the absence pANCA in the sample.

17. The method of claim 16, wherein the sample comprises human blood serum.

18. The method of claim 16, wherein the specific binding agent for pANCA is labeled with a detectable marker.

19. The method of claim 18, wherein the specific binding agent for pANCA comprises antibody material specific for the class determining portion of pANCA.

20. The method of claim 19, wherein the specific binding agent comprises mouse anti-human IgG.

21. The method of claim 20, wherein the specific binding agent further comprises anti-mouse antibody material specific for the class determining portion of the mouse anti-human IgG, wherein the anti-mouse antibody material is labeled with a detectable marker.

22. The method of claim 16, wherein the neutrophil and the specific binding agent for pANCA are simultaneously contacted with the sample.

23. The method of claim 16, wherein the neutrophil and the specific binding agent for pANCA are sequentially contacted with the sample.

24. The method of claim 1, wherein detecting the presence or absence of pANCA in a sample comprises:

(a) contacting a first sample from the patient with neutrophil and a specific binding agent for pANCA under conditions suitable to form a pANCA-containing immune complex;

(b) detecting the presence or absence of pANCA-containing immune complex formed in step (a), wherein the absence of pANCA-containing immune complex indicates the absence of pANCA in the sample;

(c) contacting a second sample with DNase-treated neutrophil and a specific binding agent for pANCA under conditions suitable to form a pANCA-containing immune complex; and (d) detecting the presence or absence of pANCA-containing immune complex formed in step (c), wherein the presence of an immune complex in step (b) and the absence of an immune complex in step (d) indicates the presence of pANCA in the sample.

25. The method of claim 24, wherein the first sample and the second sample comprise the same type of biological fluid or tissue.

26. The method of claim 25 wherein the first sample and the second sample comprise human blood serum.

27. The method of claim 24, wherein the specific binding agent for pANCA is labeled with a detectable marker.

28. The method of claim 27 wherein the specific binding agent for pANCA comprises antibody material specific for the class determining portion of pANCA.

29. The method of claim 28, wherein the specific binding agent comprises mouse anti-human IgG.

30. The method of claim 29, wherein the specific binding agent further comprises anti-mouse antibody material specific for the class determining portion of the mouse anti-human IgG, wherein the anti-mouse antibody material is labeled with a detectable marker.

31. The method of claim 24, wherein the neutrophil and the specific binding agent for pANCA are simultaneously contacted with the sample.

32. The method of claim 24, wherein the neutrophil and the specific binding agent for pANCA are sequentially contacted with the sample.

33. A method of screening a patient for Crohn's disease ("CD") and ulcerative colitis ("UC"), comprising:

(a) contacting a first sample with anti-VH3-15 idiotypic antibody material under conditions suitable to form a VH3-15 autoantibody-containing immune complex;

(b) determining the amount of VH3-15 autoantibody in the first sample by detecting the amount of VH3-15 autoantibody-containing complex formed in step (a);

(c) contacting a second sample from the patient with neutrophil and a specific binding agent for pANCA under conditions suitable to form a pANCA-containing immune complex;

(d) detecting the presence or absence of pANCA-containing immune complex formed in step (c), wherein the absence of pANCA-containing immune complex indicates the absence of pANCA;

(e) contacting a third sample with DNase-treated neutrophil and a specific binding agent for pANCA under conditions suitable to form a pANCA-containing immune complex; and (f) detecting the presence or absence of pANCA-containing immune complex formed in step (e), wherein the presence of an immune complex in step (d) and the absence of an immune complex in step (e) indicates the presence of pANCA, and wherein an amount of VH3-15 autoantibody in the sample which exceeds the amount of VH3-15 autoantibody in a VH3-15 assay control and the absence of pANCA indicates CD, and wherein an amount of VH3-15 autoantibody in the sample that does not exceed the amount of VH3-15 autoantibody in a VH3-15 assay control and the presence of pANCA indicates UC.

34. The method of claim 33, wherein the second sample and the third sample comprise the same type of biological fluid or tissue.

35. The method of claim 34, wherein the second sample and the third sample comprise human blood serum.

36. The method of claim 33, wherein the first sample is human blood serum.

37. The method of claim 36, wherein the first sample is also used as the second sample.

38. A kit for screening a patient for ulcerative colitis and Crohn's disease, comprising anti-VH3-15 idiotypic antibody material and a reagent selected from the group consisting of neutrophil and DNase treated neutrophil.

39. The kit of claim 38, wherein the reagent is neutrophil.

40. The kit of claim 39, wherein the neutrophil is immobilized on a solid matrix.

41. The kit of claim 40, further comprising a VH3-15 assay control.

42. The kit of claim 41, further comprising cell surface antigen.

43. The kit of claim 42, wherein the cell surface antigen is immobilized on a solid matrix.

44. The kit of claim 43, wherein the cell surface antigen is bound to *Campylobacter jejuni* cell membrane.

45. The kit of claim 43, wherein the cell surface antigen is bound to human erythrocyte cell membrane.

46. The kit of claim 45, wherein the erythrocyte cell membrane is pre-treated with bromelase.

47. The kit of claim 45, further comprising bromelase.

48. The kit of claim 46, further comprising DNase.

49. The kit of claim 48, further comprising a specific binding agent for pANCA.

50. The kit of claim 49, wherein the specific binding agent for pANCA comprises anti-IgG.

51. The kit of claim 50, further comprising a detectable marker.

52. The kit of claim 51, wherein the detectable marker is an enzyme, the kit further comprising an enzyme substrate for the enzyme.

53. The kit of claim 38, wherein the reagent is DNase-treated neutrophil.

54. The kit of claim 53, wherein the neutrophil is immobilized on a solid matrix.

55. The kit of claim 54, further comprising a VH3-15 assay control.

56. The kit of claim 55, further comprising cell surface antigen.

57. The kit of claim 56, wherein the cell surface antigen is immobilized of a solid matrix.

58. The kit of claim 57, wherein the cell surface antigen is bound to *Campylobacter jejuni* cell membrane.

59. The kit of claim 57, wherein the cell surface antigen is bound to human erythrocyte cell membrane.

60. The kit of claim 59, wherein the erythrocyte cell membrane is pre-treated with bromelase.

61. The kit of claim 59, further comprising bromelase.

62. The kit of claim 61, further comprising DNase.

63. The kit of claim 62, further comprising a specific binding agent for pANCA.

64. The kit of claim 63, wherein the specific binding agent for pANCA comprises anti-IgG.

65. The kit of claim 63, further comprising a detectable marker.

66. The kit of claim 65, wherein the detectable marker is an enzyme, the kit further comprising an enzyme substrate for the enzyme.

* * * * *

UNITED STATES PATENT AND TRADEMARK OFFICE
CERTIFICATE OF CORRECTION

PATENT NO. : 5,691,151
DATED : Nov. 25, 1997
INVENTOR(S) : Braun et al.

It is certified that error appears in the above-indentified patent and that said Letters Patent is hereby corrected as shown below:

Title page, [73], please add --and Cedars-Sinai Medical Center, Los Angeles, Calif.--

Column 6, line 39, please delete "being therapeutic" and replace therefor with --therapeutic--.

Column 9, line 24, please delete "employ" and replace therefor with --employed--.

Column 10, line 18, please delete "increase" and replace therefor with --increased--.

Column 10, line 49, please delete "be photograph" and replace therefor with --be a photograph--.

Column 12, line 18, please delete "forms is" and replace therefor with --forms as--.

Column 12, line 39, please delete "illustrative" and replace therefor with --illustrated--.

Column 14, line 51, please delete "contact the cell" and replace therefor with --contact of the cell--.

UNITED STATES PATENT AND TRADEMARK OFFICE
CERTIFICATE OF CORRECTION

Page 2 of 3

PATENT NO. : 5,691,151
DATED : Nov. 25, 1997
INVENTOR(S) : Braun et al.

It is certified that error appears in the above-indentified patent and that said Letters Patent is hereby corrected as shown below:

Column 17, line 5, please delete "agent are" and replace therefor with --agents are--.

Column 17, line 56, please delete "absence pANCA" and replace therefor with --absence of pANCA--.

Column 22, line 29, please delete "such a protein" and replace therefor with --such as a protein--.

Column 22, line 33, please delete "a reagent" and replace therefor with --reagent--.

Column 22, line 57, please delete "sequence" and replace therefor with --sequences--.

Column 29, line 11, please delete "incubate" and replace therefor with --incubated--.

Column 31, line 8, please delete "incubate" and replace therefor with --incubated--.

Column 31, line 67, please delete "Gathersburg" and replace therefor with --Gaithersburg--.

UNITED STATES PATENT AND TRADEMARK OFFICE
CERTIFICATE OF CORRECTION

PATENT NO.   : 5,691,151
DATED        : Nov. 25, 1997
INVENTOR(S)  : Braun et al.

It is certified that error appears in the above-indentified patent and that said Letters Patent is hereby corrected as shown below:

Column 43, line 7, please delete "absence pANCA" and replace therefor with --absence of pANCA--.

Signed and Sealed this

Twenty-third Day of March, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 501 base pairs
        ( B ) TYPE: nucleic acid
        ( C ) STRANDEDNESS: both
        ( D ) TOPOLOGY: linear ( i i ) MOLECULE TYPE: DNA (genomic)

( i v ) ANTI-SENSE: NO ( i x ) FEATURE:
    ( A ) NAME/KEY: CDS
    ( B ) LOCATION: 161..460

( i x ) FEATURE:
    ( A ) NAME/KEY: intron
    ( B ) LOCATION: group(47..149, 470..492)

( i x ) FEATURE:
    ( A ) NAME/KEY: misc_feature
    ( B ) LOCATION: 247..261
    ( D ) OTHER INFORMATION: /function="Structural domain of
        protein product"
        / product= "Complement Determining Region I - CDRI"

( i x ) FEATURE:
    ( A ) NAME/KEY: misc_feature
    ( B ) LOCATION: 308..364
    ( D ) OTHER INFORMATION: /function="Structural domain of
        protein product"
        / product= "Complement Determining Region II - CDR II"

( x i ) SEQUENCE DESCRIPTION: SEQ ID NO:1:

```
ATGGAGTTTG GGCTGAGCTG GATTTTCCTT GCTGCTATTT TAAAAGGTGA TTTATGGAGA          60

ACTAGAGAGA TTAAGTGTGA GTGAACGTGA GTGAGAGAAA CAGTGGATAT GTGTGGCAGT         120

TTCTGAACTT AGTGTCTCTG TGTTTGCAGG TGTCCAGTGT GAG GTG CAG CTG GTG          175
                                             Glu Val Gln Leu Val
                                              1               5

GAG TCT GGG GGA GGC TTG GTA AAG CCT GGG GGG TCC CTT AGA CTC TCC          223
Glu Ser Gly Gly Gly Leu Val Lys Pro Gly Gly Ser Leu Arg Leu Ser
                    10                  15                  20

TGT GCA GCC TCT GGA TTC ACT TTC AGT AAC TCC TCG ATG AGC TGG GTC          271
Cys Ala Ala Ser Gly Phe Thr Phe Ser Asn Ser Ser Met Ser Trp Val
                25                  30                  35

CGC CAG GCT CCA GGG AAA GGG CTG GAG TGG GTT GGC CGT ATT AAA AGC          319
Arg Gln Ala Pro Gly Lys Gly Leu Glu Trp Val Gly Arg Ile Lys Ser
            40                  45                  50

AAA ACT GAT GGT GGG ACA ACA GAC TAC GCT GCA CCC GTG AAA GGC AGA          367
Lys Thr Asp Gly Gly Thr Thr Asp Tyr Ala Ala Pro Val Lys Gly Arg
        55                  60                  65

TTC ACC ATC TCA AGA GAT GAT TCA AAA AAC TCA CTG TAT CTG CAA ATG          415
Phe Thr Ile Ser Arg Asp Asp Ser Lys Asn Ser Leu Tyr Leu Gln Met
 70                 75                  80                  85

AAC AGC CTG AAA ACC GAG GAC ACA GCC GTG TAT TAC TGT ACC ACA              460
Asn Ser Leu Lys Thr Glu Asp Thr Ala Val Tyr Tyr Cys Thr Thr
                90                  95                 100

GACACAGCGA GGGGAGGTCA GTGTGAGCCC GGACACAAAC C                            501
```

( 2 ) INFORMATION FOR SEQ ID NO:2:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ser
                20                  25                  30

Ser Met Ser Trp Val Arg Gln Ala Pro Gly Lys Gly Leu Glu Trp Val
```

```
                    3 5                       4 0                         4 5
Gly  Arg  Ile  Lys  Ser  Lys  Thr  Asp  Gly  Gly  Thr  Thr  Asp  Tyr  Ala  Ala
     5 0                       5 5                      6 0

Pro  Val  Lys  Gly  Arg  Phe  Thr  Ile  Ser  Arg  Asp  Asp  Ser  Lys  Asn  Ser
6 5                       7 0                      7 5                      8 0

Leu  Tyr  Leu  Gln  Met  Asn  Ser  Leu  Lys  Thr  Glu  Asp  Thr  Ala  Val  Tyr
               8 5                            9 0                      9 5

Tyr  Cys  Thr  Thr
               1 0 0
```

( 2 ) INFORMATION FOR SEQ ID NO:3:

( i ) SEQUENCE CHARACTERISTICS:
        ( A ) LENGTH: 100 amino acids
        ( B ) TYPE: amino acid
        ( C ) STRANDEDNESS: single
        ( D ) TOPOLOGY: unknown ( i i ) MOLECULE TYPE: peptide ( v ) FRAGMENT TYPE: N-terminal ( i x ) FEATURE:
        ( A ) NAME/KEY: Region
        ( B ) LOCATION: 31..36
        ( D ) OTHER INFORMATION: /label=CDRI
            / note= "Complement Determining Region I"

( i x ) FEATURE:
        ( A ) NAME/KEY: Region
        ( B ) LOCATION: 50..69
        ( D ) OTHER INFORMATION: /label=CDRII
            / note= "Complement Determining Region II"

( x i ) SEQUENCE DESCRIPTION: SEQ ID NO:3:

```
Glu  Val  Gln  Leu  Val  Glu  Ser  Gly  Gly  Gly  Leu  Val  Lys  Pro  Gly  Arg
1                        5                         1 0                     1 5

Ser  Leu  Arg  Leu  Ser  Cys  Ala  Ala  Ser  Gly  Phe  Thr  Phe  Ser  Asn  Ala
               2 0                       2 5                      3 0

Trp  Met  Ser  Trp  Val  Arg  Gln  Ala  Pro  Gly  Lys  Gly  Leu  Glu  Trp  Val
          3 5                       4 0                      4 5

Gly  Arg  Ile  Lys  Ser  Lys  Thr  Asp  Gly  Gly  Thr  Thr  Asp  Tyr  Ala  Ala
     5 0                       5 5                      6 0

Pro  Val  Lys  Gly  Arg  Phe  Thr  Ile  Ser  Arg  Asp  Asp  Ser  Lys  Asn  Thr
6 5                       7 0                      7 5                      8 0

Leu  Tyr  Leu  Gln  Met  Asn  Ser  Leu  Lys  Ala  Glu  Asp  Thr  Ala  Val  Tyr
               8 5                            9 0                      9 5

Tyr  Cys  Thr  Thr
               1 0 0
```

( 2 ) INFORMATION FOR SEQ ID NO:4:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: unknown ( i i ) MOLECULE TYPE: peptide ( v ) FRAGMENT TYPE: N-terminal ( i x ) FEATURE:
        ( A ) NAME/KEY: Region
        ( B ) LOCATION: 28..33
        ( D ) OTHER INFORMATION: /label=CDRI
            / note= "Complement Determining Region I"

( i x ) FEATURE:
　　( A ) NAME/KEY: Region
　　( B ) LOCATION: 47..66
　　( D ) OTHER INFORMATION: /label=CDRII
　　　　/ note= "Complement Determining Region II"

( i x ) FEATURE:
　　( A ) NAME/KEY: Region
　　( B ) LOCATION: 98..125
　　( D ) OTHER INFORMATION: /label=CDRIII
　　　　/ note= "Complement Determining Region III"

( x i ) SEQUENCE DESCRIPTION: SEQ ID NO:4:

| Leu | Val | Glu | Ser | Arg | Gly | Gly | Leu | Val | Lys | Pro | Gly | Arg | Ser | Leu | Arg |
|---|---|---|---|---|---|---|---|---|---|---|---|---|---|---|---|
| 1 |  |  |  | 5 |  |  |  |  | 10 |  |  |  |  | 15 |  |
| Leu | Ser | Cys | Ala | Ala | Ser | Gly | Phe | Thr | Phe | Ser | Asn | Ala | Trp | Met | Ser |
|  |  |  | 20 |  |  |  |  | 25 |  |  |  |  | 30 |  |  |
| Trp | Val | Arg | Gln | Ala | Pro | Gly | Lys | Gly | Leu | Glu | Trp | Val | Gly | Arg | Ile |
|  |  | 35 |  |  |  |  | 40 |  |  |  |  | 45 |  |  |  |
| Lys | Ser | Lys | Thr | Asp | Gly | Gly | Thr | Thr | Asp | Tyr | Ala | Ala | Pro | Val | Lys |
|  | 50 |  |  |  |  | 55 |  |  |  |  |  | 60 |  |  |  |
| Gly | Arg | Phe | Thr | Ile | Ser | Arg | Asp | Asp | Ser | Lys | Asn | Thr | Leu | Tyr | Leu |
| 65 |  |  |  |  | 70 |  |  |  |  | 75 |  |  |  |  | 80 |
| Gln | Met | Asn | Ser | Leu | Lys | Ala | Glu | Asp | Thr | Ala | Val | Tyr | Tyr | Cys | Thr |
|  |  |  |  | 85 |  |  |  |  | 90 |  |  |  |  | 95 |  |
| Thr | Trp | Tyr | Pro | Asp | Ile | Leu | Asp | Ser | Cys | Tyr | Ala | Ser | Tyr | Phe | Asp |
|  |  |  | 100 |  |  |  |  | 105 |  |  |  |  | 110 |  |  |
| Tyr | Trp | Gly | Gln | Gly | Thr | Leu | Val | Thr | Val | Ser | Ser | Gly |  |  |  |
|  |  | 115 |  |  |  |  | 120 |  |  |  |  | 125 |  |  |  |